United States Patent
Labib et al.

(10) Patent No.: US 10,285,865 B2
(45) Date of Patent: May 14, 2019

(54) DRUG-RELEASING DEVICE USABLE IN MUCOSAL BODY CAVITIES

(71) Applicant: Princeton Trade & Technololgy, Inc., Princeton, NJ (US)

(72) Inventors: Mohamed E. Labib, Princeton, NJ (US); Stanislav S. Dukhin, Goldens Bridge, NY (US)

(73) Assignee: Novaflux Inc., Princeton, NJ (US)

( * ) Notice: Subject to any disclaimer, the term of this patent is extended or adjusted under 35 U.S.C. 154(b) by 466 days.

(21) Appl. No.: 14/702,211

(22) Filed: May 1, 2015

(65) Prior Publication Data
US 2016/0022497 A1    Jan. 28, 2016

Related U.S. Application Data

(60) Provisional application No. 61/987,533, filed on May 2, 2014, provisional application No. 62/155,123, filed on Apr. 30, 2015.

(51) Int. Cl.
*A61F 2/00* (2006.01)
*A61M 31/00* (2006.01)
(Continued)

(52) U.S. Cl.
CPC ............. *A61F 11/002* (2013.01); *A61L 27/54* (2013.01); *A61L 27/56* (2013.01); *A61L 27/58* (2013.01);
(Continued)

(58) Field of Classification Search
CPC .................. A61F 11/002; A61F 2/0077; A61F 2250/0067; A61F 2250/0068; A61L 27/54; A61L 2300/406
See application file for complete search history.

(56) References Cited

U.S. PATENT DOCUMENTS 4,405,306 A    9/1983  Cardarelli
4,863,444 A    9/1989  Blomer
(Continued)

FOREIGN PATENT DOCUMENTS

WO    WO 2007/149771 A2    12/2007
WO    WO 2009/001358 A2    12/2008
(Continued)

OTHER PUBLICATIONS

Merkus, Henk Gl. "Particle size, size distributions and shape." Particle Size Measurements (2009): 13-42. APA.
(Continued)

*Primary Examiner* — Leslie R Deak
(74) *Attorney, Agent, or Firm* — Merchant & Gould P.C.

(57) ABSTRACT

A tympanostomy tube containing a polymeric material and a drug is described. The polymeric material may comprise a non-resorbable polymer and a water-soluble polymer. The drug may be released when the device is contacted by an aqueous liquid such as middle ear exudate during otitis media. The implant may contain sufficient drug to treat multiple episodes of otitis media or to catch subsequent episodes in their early stages as a prophylactic. The device may be hydrophilic and further may contain a surfactant. The implant may be porous. The implant may have enhanced surface area at places exposed to middle ear liquid and may have enlarged mass so as to contain an increased total amount of drug. Intentional reorientation of the patient's head may aid in moving drug-containing liquid around the middle ear cavity. Similar implants can be used in other mucosal cavities.

28 Claims, 17 Drawing Sheets

(51) Int. Cl.

| | | |
|---|---|---|
| *A61L 27/58* | (2006.01) | |
| *A61L 27/54* | (2006.01) | |
| *A61L 31/16* | (2006.01) | |
| *A61L 31/14* | (2006.01) | |
| *A61L 31/04* | (2006.01) | |
| *A61L 27/56* | (2006.01) | |
| *A61F 11/00* | (2006.01) | |

(52) U.S. Cl.
CPC .............. *A61L 31/04* (2013.01); *A61L 31/146* (2013.01); *A61L 31/16* (2013.01); *A61F 2/0077* (2013.01); *A61F 2250/0067* (2013.01); *A61F 2250/0068* (2013.01); *A61L 2300/21* (2013.01); *A61L 2300/406* (2013.01); *A61L 2300/41* (2013.01); *A61L 2300/602* (2013.01); *A61L 2430/14* (2013.01); *A61M 31/002* (2013.01)

(56) References Cited

U.S. PATENT DOCUMENTS

| | | | |
|---|---|---|---|
| 5,026,378 | A | 6/1991 | Goldsmith, III |
| 5,302,397 | A | 4/1994 | Amsden et al. |
| 5,350,580 | A | 9/1994 | Muchow et al. |
| 5,489,286 | A | 2/1996 | Cinberg et al. |
| 5,512,055 | A | 4/1996 | Domb |
| 5,601,835 | A | 2/1997 | Sabel et al. |
| 5,633,000 | A | 5/1997 | Grossman |
| 6,120,484 | A | 9/2000 | Silverstein |
| 6,361,526 | B1 | 3/2002 | Reisdorf et al. |
| 6,379,323 | B1 | 4/2002 | Patterson |
| 6,589,286 | B1 | 7/2003 | Litner |
| 6,641,831 | B1 | 11/2003 | Schierholz |
| 6,676,930 | B2 | 1/2004 | Mautone |
| 6,723,333 | B1 | 4/2004 | Albers et al. |
| 8,187,254 | B2 | 5/2012 | Hissink et al. |
| 8,318,817 | B2 | 11/2012 | Lichter et al. |
| 8,366,660 | B2 * | 2/2013 | Wang .................. A61K 31/337 604/99.04 |
| 8,747,883 | B2 | 6/2014 | Labib et al. |
| 9,326,943 | B1 | 5/2016 | Skovlund |
| 2004/0024018 | A1 | 2/2004 | Kanikanti |
| 2006/0018948 | A1 | 1/2006 | Guire et al. |
| 2007/0254035 | A1 | 11/2007 | Hao et al. |
| 2008/0318918 | A1 | 12/2008 | Campbell et al. |
| 2009/0076480 | A1 | 3/2009 | Pudleiner et al. |
| 2009/0138074 | A1 * | 5/2009 | Freyman .............. A61L 27/3633 623/1.38 |
| 2009/0171464 | A1 | 7/2009 | Imhof |
| 2009/0171465 | A1 | 7/2009 | Bacy-Couto et al. |
| 2009/0263460 | A1 | 10/2009 | McDonald |
| 2009/0311304 | A1 | 12/2009 | Borck et al. |
| 2010/0121285 | A1 | 5/2010 | Illi et al. |
| 2010/0174366 | A1 | 7/2010 | Avior |
| 2010/0273864 | A1 | 10/2010 | Lichtner et al. |
| 2011/0300202 | A1 | 12/2011 | Labib |
| 2012/0165795 | A1 * | 6/2012 | Seiler .................. A61K 9/0024 604/890.1 |
| 2013/0129807 | A1 * | 5/2013 | Devore ................. A61K 47/42 424/443 |
| 2014/0107423 | A1 | 4/2014 | Yaacobi |
| 2015/0351967 | A1 | 12/2015 | Lim et al. |
| 2015/0352260 | A1 | 12/2015 | Labib et al. |

FOREIGN PATENT DOCUMENTS

| | | |
|---|---|---|
| WO | WO 2009/035562 A2 | 3/2009 |
| WO | WO 2009/051819 A1 | 4/2009 |
| WO | WO 2009/129439 | 10/2009 |
| WO | WO2011152857 | 12/2011 |
| WO | WO2012128720 | 9/2012 |
| WO | WO 2014/051524 A1 | 4/2014 |
| WO | WO2014051524 | 4/2014 |

OTHER PUBLICATIONS

DuPont™ Elvax® EVA resins for Adhesives, Sealants and Wax Bends. ©2012.
Labib et al., "Colloids and Surfaces A." Physicochem. Eng. Aspects 354 p. 331-337, (2010).
Lee et al., "Overview of Controlled-Release Drug Delivery," p. 1-13 in "Controlled-Release Technology," ACS Symposium Series 348 Amer. Chem. Society Washington DC 1987.
Scheirholz et al., "Controlled Release of Antibiotics From Biomedical Polyurethanes: Morphological and Structural Features," Biomaterials, 18 (12), 839-844 (1997).
Sprockel et al., "A Melt Extrusion Process for Manufacturing Matrix Drug Delivery Systems," Int. J. of Pharmaceutics, vol. 155, pp. 191-199 (1997).
Peter D. Eimas, et al.; Otitis Media, Hearing Loss, and Child Development: a NICHD Conference Summary; Public Health Reports May-Jun. 1986, vol. 101, No. 3 pp. 289-293.
Lauren Bakaletz; Otitis Media—Polymicrobial Diseases—NCBI Bookshelf Chap. 14 Otitis Media; 2002, ASM Press; https://www.ncbi.nlm.nih.gov/books/NBK2482/?report=printable.
Ramsey Alsarraf, et al.; Measuring the Indirect and Direct Costs of Acute Otitis Media; Arch. Otolaryngol. Head Neck Surg vol. 125, Jan. 1999 pp. 12-18.
Aaron T. Curns, et al.; Outpatient and Hospital Visits Associated With Otitis Media Among American Indian and Alaska Native . . . Pediatrics vol. 109 No. 3 Mar. 2002, pp. 1-6.
Ellen R, Wald, et al.; Frequency and severity of infections in day care; The Journal of Pediatrics, vol. 112, No. 4, pp. 540-546. Apr. 1988.
David W. Teele, et al.;Otitis Media in Infancy and Intellectual Ability, School Achievement, Speech, and Language at Age . . . The Journal of Infectious Diseases 1990;162:685-694.
Richard M. Rosenfeld et al.; Clinical practice guideline: Otitis media with effusion; Otolaryngology—Head and Neck Surgery, vol. 130, No. 5, May 2004.
Collette Ah-Tye, et al.; Otorrhea in Young Children After Tympanostomy-Tube Placement for Persistent Middle-Ear . . . Pediatrics, vol. 107, No. 6, pp. 1251-1258 Jun. 2001.
Mohamed E. Labib, et al.; The long-term release of antibiotics from monolithic nonporous polymer . . . Colloids and Surfaces A: Physicochem. Eng. Aspects 354 (2010) 331-337.
Stanislav S. Dukhin, et al.; Theory of effective drug release from medical implants based on the Higuchi . . . Colloids and Surfaces A: Physicochem. Eng. Aspects 409 (2012) 10-20.
Minori Matsumoto et al.; Mutations in the gyrA and parC genes and in vitro activities of fluoroquinolones . . . International Journal of Antimicrobial Agents 40 (2012) 440-444.
S. M. Tambe, et al.; In vitro evaluation of the risk of developing bacterial resistance to antiseptics and antibiotics.Journal of Antimicrobial Chemotherapy (2001) 47, 589-598.
Paul Stoodley, et al.; Characterization of a mixed MRSA/MRSE biofilm in an explanted total ankle arthroplasty; FEMS Immunol Med Microbiol 62 (2011) 66-74.
Ellen M. Mandel, et al.; Acute otorrhea: Bacteriology of a common complication of tympanostomy tubes; Ann Otol Rhinol Laryngol 103: 1994 (pp. 713-718).
Farrel J Buchinsky, et al.; Virulence phenotypes of low-passage clinical isolates of Nontypeable . . . BMC Microbiology 2007, 7:56 http://www.biomedcentral.com/1471-2180/7/56.
Wynn Kapit et al.; The Anatomy Coloring Book, Third Edition; p. 99; 1994.
Rodney M. Donlan, et al.; Biofilms: Survival mechanisms of clinically relevant mircoorganisms; Clinical Microbiology Reviews, Apr. 2002, vol. 15, No. 2. p. 167-193.
John Newman; Mass transfer to the rear of a cylinder at high Schmidt numbers; I&EC Fundamentals vol. 8 No. 3 ; pp. 553-557; Aug. 1969.
Daniel Bonn, et al.; Wetting and Spreading; Reviews of modern physics, vol. 81, Apr.-Jun. 2009, pp. 739-805.
Jens Eggers; Hydrodynamic Theory of Forced Dewetting; Physical Review Letters, vol. 93, No. 9, 2004.

(56) References Cited

OTHER PUBLICATIONS

Jens Eggers; Existence of receding and advancing contact lines; Physics of Fluids 17, 082106 2005.
Y.I. Frenkel; On the behavior of liquid drops on a solid surface 1. The sliding of drops on an inclined surface; J. Exptl. Theoret. Phys. (USSR), 18, 659, 1948.
Shinichi Sano, et al.; Micropathologic Changes of Pars Tensa in Children With Otitis Media With Effusion; Arch Otolaryngol Head Neck Surg. 1994;120:815-819.
Ellen M. Mandel et al.; Myringotomy With and Without Tympanostomy Tubes for Chronic Otitis Media With Effusion; Arch Otolaryngol Head Neck Surg. 1989;115:1217-1224.
David J. Arnold, et al.; Permeability of tympanotomy tubes to ototopical preparations; Otolaryngology—Head and Neck Surgery, Jul. 1999, pp. 35-37.
Richard M. Rosenfeld; Surgical prevention of otitis media; Vaccine 19 (2001) S134-S139.
Elizabeth R. Ramos, et al.; Clinical effectiveness and risk of emerging resistance associated with prolonged use of . . . ; Crit Care Med 2011 vol. 39, No. 2, pp. 245-251.
Otavio B. Piltcher, et al.; A rat model of otitis media with effusion caused by eustachian tube obstruct . . . ;Otolaryngology—Head and Neck Surgery, vol. 126 No. 5, pp. 490-498.
Patricia A. Hebda, et al.; Cytokine Profiles in a Rat Model of Otitis Media With Effusion Caused by Eustachian Tube . . . ; Laryngoscope 112: Sep. 2002, pp. 1657-1662.
Rodrigo C. Silva, et al.; Novel rat model of tympanostomy tube otorrhea; International Journal of Pediatric Otorhinolaryngology 76 (2012) 179-182.
Phillip H. Gallo, et al.; Demonstration of Bacillus cereus in Orthopaedic-Implant-Related Infection with Use of a Multi-Primer . . . ; J Bone Joint Surg Am. 2011;93:e85(1-6).
Patricia A. Hebda, et al.; Effects of Ciprofloxacin-Dexamethasone on Myringotomy Wound Healing; Laryngoscope 117: Mar. 2007, pp. 552-528.
Sharon Freeman, et al.; Objective Method for Differentiating Between Drug-Induced Vestibulotoxicity and Cochleotoxicity; Otology & Neurotology, vol. 22, No. 1, 2001, pp. 70-75.
Michael L. Forbes, et al.; Strain-Specific Virulence Phenotypes of *Streptococcus pneumoniae* Assessed Using the Chinchilla . . . ; PLoS One, Apr. 2008, vol. 3, Is. 4, e1969, p. 1-11.
Search Report and Written Opinion for PCT/US2015/028925 dated Oct. 5, 2015.
Partial International Search Report for Application No. PCT/US2015/028925 dated Jul. 27, 2015.
International Search Report and Written Opinion for Application No. PCT/US2015/028925 dated Oct. 5, 2015.
Roland, Peter S., et al. "Topical ciprofloxacin/dexamethasone is superior to ciprofloxacin alone in pediatric patients with acute otitis media and otorrhea through tympanostomy tubes." The Laryngoscope 113.12 (2003); 2116-2122.
Crowley, Michael M., et al. "Pharmaceutical applications of hot-melt extrusion: part 1." Drug development and industrial pharmacy 33.9 (2007): 909-926. (Year: 2007).

\* cited by examiner

Grooves

Holes

Grooves

Grooves and holes

Projections

Figure 10A
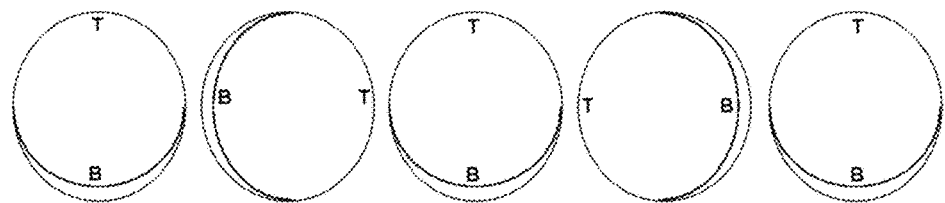
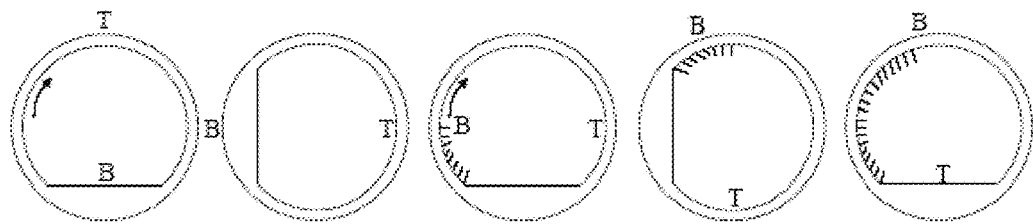
Figure 10B

Figure 11C
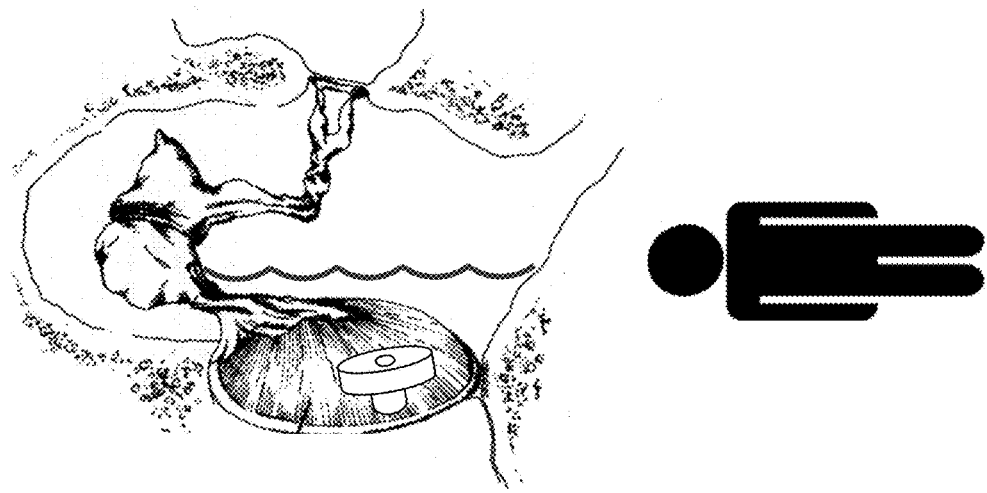
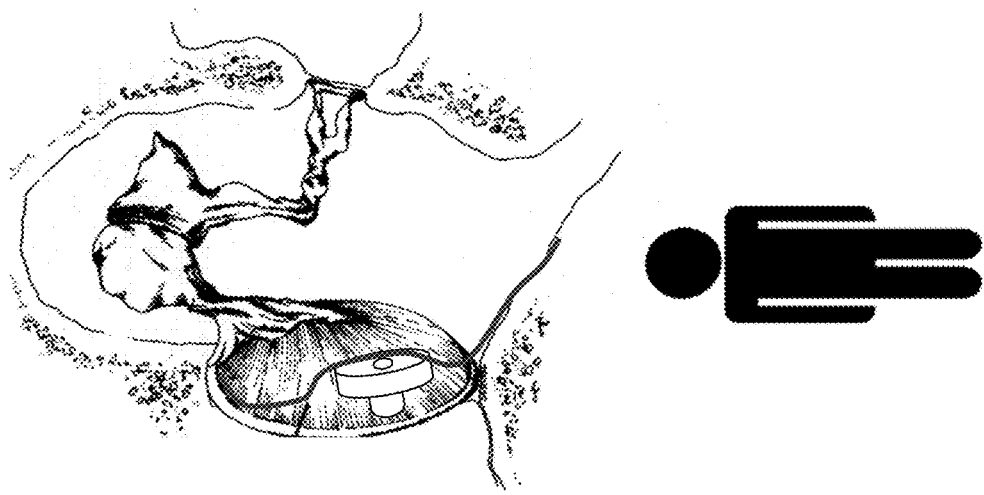
Figure 11D

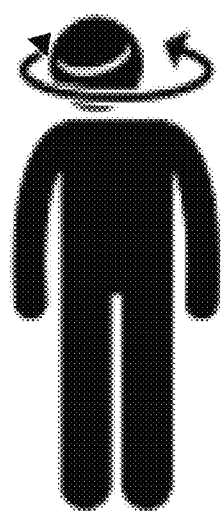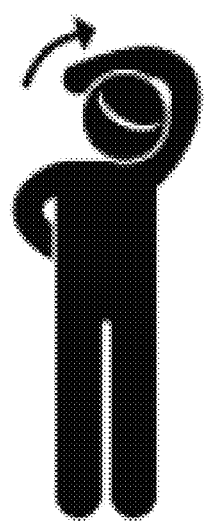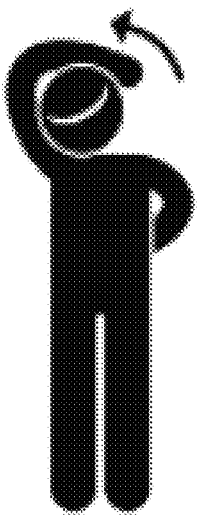
Figure 11E        Figure 11F
Figure 11G

DRUG-RELEASING DEVICE USABLE IN MUCOSAL BODY CAVITIES

CROSS-REFERENCE TO RELATED APPLICATIONS

This application claims priority, to the extent appropriate, to U.S. Provisional Application No. 61/987,533 filed on May 2, 2014 and U.S. Provisional Application No. 62/155,123 filed on Apr. 29, 2015. The entire disclosures of U.S. Provisional Application No. 61/987,533 and U.S. Provisional Application No. 61/155,123 are incorporated herein by reference.

FIELD OF THE INVENTION

Embodiments of the invention pertain to drug delivery and to infections of the middle ear, the inner ear, sinuses and to other mucosal cavities.

BACKGROUND

Middle ear infection (Otitis Media or OM) is the most common infection in young children in the western world. It is estimated that about 30% of antibiotics prescribed in the United States is used to treat otitis media in children. This widespread use of antibiotics has significant consequences arising from the development of resistant microorganisms. Otitis Media is the most common reason for parents to be absent from work to take care of their children, with a cost to the economy of several billion dollars annually.

In the region of the infection, liquid exudate is formed due to inflammation of the middle ear as the result of the infection. This liquid or fluid can occupy a portion of the middle ear and in some cases can fill the entire middle ear cavity creating local high pressure. The secreted liquid in the middle ear cannot drain through the Eustachian tube because the Eustachian tube becomes blocked due to swelling of the adenoids and adjacent tissues. Accumulation of fluid in middle ear is associated with a high level of discomfort and pain, and is often associated with loss of balance in young children.

Typically the first approach to treating Otitis Media is systemic antibiotics. If the antibiotic treatment is not successful and if infection recurred more frequently, the standard of care intervention is myringotomy with tube placement, in which a tympanostomy tube (TT) is placed through the eardrum (tympanic membrane), normally under complete anesthesia. A tympanostomy tube allows fluid to drain out of middle ear and functions to ventilate and equalize the pressure with the outside atmosphere. Because of these functions, tympanostomy tubes are often referred to as vent tubes or simply ear tubes. The standard of care in the United States is to prescribe antibiotic otic drops after myringotomy. The most commonly prescription includes the antibiotic ciprofloxacin and the anti-inflammatory compound dexamethasone. The most recognized otic drops prescription in United States is Ciprodex® made by Alcon Laboratories. Ciprofloxacin in Ciprodex is a 0.3% suspension of the hydrochloride salt, which has a high solubility in water. Otic drops are typically administered with the patient lying on his or her side with the infected ear facing upward, so that the liquid of the administered ear drops descends by gravity and assisted by pumping action through the tympanostomy tube into the middle ear.

Otitis media is the leading cause of acquired hearing loss in the pediatric population, and is also the most common reason an ill child under age 15 visits a pediatrician or emergency room, with 24.5 million office visits in 1990 alone. The cost of diagnosing and treating Otitis Media exceeds $5 billion annually in the United States. Otitis Media is a disease that disproportionately affects minority populations, especially Native American children, who have three times the incidence of Otitis Media as whites. Otitis Media prevalence is also significantly higher with children in daycare, who receive a tympanostomy tube placement at many times the rate of young children who do not attend daycare. Otitis Media has consequences for women in the workforce as well, since women typically remain the primary caregivers for these children, and they are often responsible for obtaining medical care. An average of one half of a workday is required for each physician visit for each Otitis Media episode. This has significant national economic consequences given that women currently make up 46% of the American workforce.

Hearing loss is the most common complication of Otitis Media, often causing moderate to severe impairment. Multiple studies have indicated that children affected by Otitis Media-related hearing loss have cognitive impairment, language skill deficits, poor school performance, and antisocial behavior. Repeated episodes of Otitis Media may lead to permanent forms of hearing loss through tympanic membrane perforation, tympanosclerosis development, ossicular disruption, and irreversible middle ear mucosal injury. In addition, chronic serious Otitis Media complicates 10% of all acute Otitis Media episodes despite appropriate medical therapy, resulting in persistent effusion and associated hearing loss.

The clinical problem of Otitis Media in its various forms thus continues to present an enormous public health challenge. Myringotomy with tympanostomy tube placement is the most effective treatment for these patients, and is the most commonly performed surgical procedure in children. In chronic otitis media with effusion (OME), tympanostomy tubes facilitate removal of persistent middle ear effusion with suction. In recurrent acute Otitis Media, tympanostomy tubes have been shown to reduce the duration, severity, and incidence of acute Otitis Media episodes. Even when an Otitis Media episode does develop, treatment options in patients with tympanostomy tubes are superior since ototopical rather than systemic antimicrobial medications may be deployed. The most common ototopical prescription includes the antibiotic ciprofloxacin and the anti-inflammatory compound dexamethasone, Ciprodex® made by Alcon Laboratories. Ciprofloxacin in Ciprodex is a 0.3% suspension of the hydrochloride salt which has a high solubility in water. Ototopical drops are typically administered with the patient lying on his or her side with the infected ear facing upward, so that the liquid of the administered ear drops descends by gravity and assisted by pumping action through the tympanostomy tube into the middle ear.

Despite the generally successful use of tympanostomy tubes in treating Otitis Media, there remain noteworthy problems in a significant percentage of children undergoing this procedure. The most common complication after tympanostomy tube placement is otorrhea, with one recent study indicating an incidence of 75% within the first post-operative year. Although most of these episodes can be effectively treated with conservative management, primarily through the targeted application of topical antibiotics, in aggregate they still represent a significant morbidity.

Even more problematic and burdensome are those patients who develop not isolated but chronic post-tympanostomy tube otorrhea (PTTO). Chronic PTTO, defined as purulent drainage lasting longer than 6 weeks despite treatment and without the presence of cholesteatoma, complicates 2-5% of all tympanostomy tube placements. The treatment of chronic PTTO remains a difficult therapeutic challenge. Systemic oral antibiotics and frequent aural toilet of the affected ear are generally recommended as initial therapy, but many patients require the use of long-term intravenous antibiotics, which itself has a 20% short-term failure rate and substantially higher recidivism over the longer term. These recalcitrant patients may ultimately require aggressive surgical intervention, typically tympanomastoidectomy.

These considerations highlight the continued difficulties of dealing with the very common problem of otitis media and its complications. Improved devices and methods would represent a highly significant advance in otolaryngology, and would have a dramatic impact on public health especially young children.

SUMMARY

In an embodiment of the invention, there may be provided a tympanostomy tube containing enough drug to treat multiple episodes of otitis media infection and to release the drug accordingly when needed.

In an embodiment of the invention, there may be provided an implant for a mucosal cavity containing enough drug to treat conditions for an extended period of time and to release the drug accordingly when needed.

In an embodiment of the invention, there may be provided an implant containing both ciprofloxacin betaine and ciprofloxacin hydrochloride, with their proportion being chosen in combination with a surface area of the implant and a Minimum Inhibitory Concentration of the drug so as to provide a desired release characteristic of the drug.

In an embodiment of the invention, there may be provided an implant containing both ciprofloxacin betaine and ciprofloxacin hydrochloride, with their proportion being chosen in combination with a surface area of the implant and a Minimum Inhibitory Concentration of the drug so as to provide a desired concentration of the drug.

In an embodiment of the invention, there may be provided an implant containing ciprofloxacin betaine and ciprofloxacin hydrochloride or both, wherein the drug is drug blended with or embedded in a polymeric material comprising a non-resorbable polymer.

In an embodiment of the invention, there may be provided a tympanostomy tube wherein the tympanostomy tube comprises a polymeric material and a drug, wherein at least one of the enlarged regions of the tympanostomy tube has a surface that has a contact angle with pure water that is less than 50 degrees.

In an embodiment of the invention, there may be provided a tympanostomy tube wherein the tympanostomy tube comprises a polymeric material and a drug and a non-ototoxic surfactant.

In an embodiment of the invention, there may be provided an implant that comprises a polymeric material, wherein at least a component of said polymeric material is nonresorbable, and a drug, and a surfactant.

In an embodiment of the invention, there may be provided a tympanostomy tube that is made of a material that contains a polymeric material and contains a drug that is releasable to an aqueous liquid when a surface of said first enlarged region is exposed to said aqueous liquid, wherein a surface of the tympanostomy tube contains any of various described surface area enhancements.

In an embodiment of the invention, there may be provided an implant for a mucosal cavity an article comprising a blend of a polymer and an active pharmaceutical ingredient, the active pharmaceutical ingredient being releasable when an aqueous liquid contacts a surface of the article, wherein a surface of the implant contains any of various described surface area enhancements.

In an embodiment of the invention, there may be provided a tympanostomy tube, wherein the tympanostomy tube comprises a composite of a polymeric material and an active pharmaceutical ingredient, and wherein a first enlarged region has a mass that is more than two times a mass of a second enlarged region.

In an embodiment of the invention, there may be provided a tympanostomy tube, wherein the tympanostomy tube contains a drug and a polymeric material, and wherein at least some of the tympanostomy tube is porous.

In an embodiment of the invention, there may be provided an implant, wherein the implant contains a drug and a polymeric material, and wherein at least some of the implant is porous.

In an embodiment of the invention, there may be provided a tympanostomy tube, wherein the first enlarged region has a first flat surface facing the second enlarged region and the second enlarged region has a second flat surface facing the first enlarged region, wherein the first flat surface is non-perpendicular to the long direction and the second flat surface is non-perpendicular to the long direction.

In an embodiment of the invention, there may be provided a tympanostomy tube, wherein a minimum distance between a first surface and a second surface is not more than 0.3 mm.

In an embodiment of the invention, there may be provided a treatment method comprising implanting a described implant in a patient, and causing or instructing said patient to change a bodily orientation in certain described ways.

BRIEF DESCRIPTION OF THE DRAWINGS

Embodiments of the invention are further described in the following drawings.

FIGS. 10A and 10B shows positions of liquid films in the middle ear cavity for various orientations of the middle ear cavity.

FIG. 11C shows a middle ear of a person in a lying-on-side position, with the middle ear cavity partially filled with liquid. FIG. 11D shows the same situation with only a liquid film present. FIG. 11E shows an instructed bodily movement of rotating the head around the spinal axis. FIG. 11F shows an instructed set of bodily positions involving leaning leftward and rightward, from an upright position. FIG. 11G shows an instructed set of bodily positions involving lying down in various orientations.

DETAILED DESCRIPTION

Figure 1:
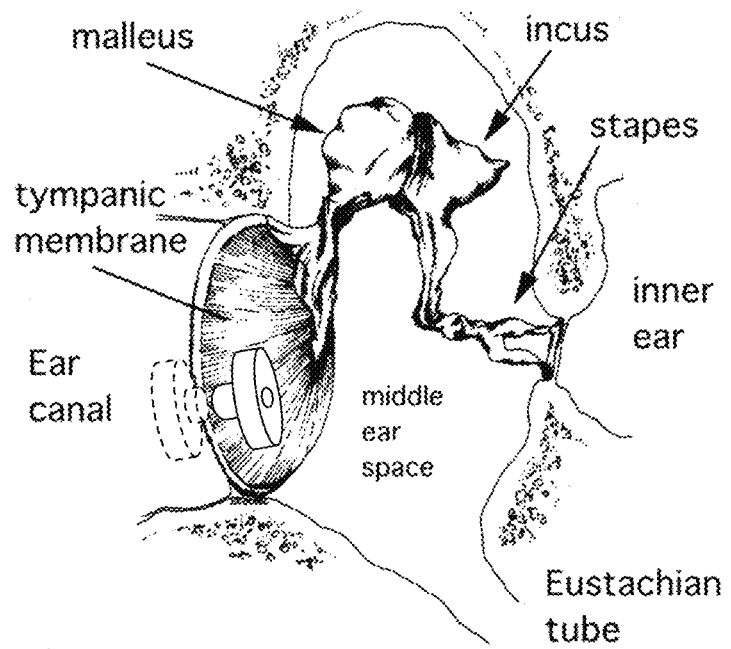
FIG. 1 shows the anatomy of the ear and typical placement of a tympanostomy tube.

Referring now to FIG. 1, there is shown typical anatomy of the human ear, and placement of a typical tympanostomy tube. It is helpful to further explain some anatomical and clinical observations about the progression of Otitis Media. It is believed, although it is not wished to be limited to this explanation, that the progression of a middle ear infection is as described here. This explanation is useful in understanding a mode of operation of embodiments of the invention.

Bacteria that are associated with Otitis Media include: *Streptococcus pneumonia; Haemophilus influenza; Branhamella catarrhalis; Staphylococcus aureus; Staphylococcus epidermidis; Diplococcus pneumonia*; and *Pseudomonas aeruginosa*. The three most commonly recovered bacteria associated with otitis media are *Streptococcus pneumoniae, Haemophilus influenzae* and *Moraxella catarrhalis*, which are all commensal within the nasopharynx; most *H. influenzae* bacteria that are isolated are non-typeable.

In a healthy condition, the middle ear region contains essentially no observable liquid, and the surface of mucosa is in equilibrium with atmospheric relative humidity. In contrast, when an infection is present, some amount of liquid exudate is present in the middle ear cavity. Nevertheless, even during an infection, often the middle ear region is only partially full of liquid, not completely filled with liquid.

It is believed that the disease progression of Otitis Media is that the infection of the middle ear starts with the existence of planktonic (free-floating, isolated) bacteria, which then proceed to form biofilm on surfaces of the middle ear cavity. Essentially all bacteria that produce middle ear infections grow on the surface middle ear mucosa as biofilms. A step in the progression is for the bacteria to form small pockets of liquid that are scattered on the surface of the mucosal tissue, such as the middle ear mucosa. After a certain period of time of continued growth of planktonic bacteria, which may be 12 to 24 to 48 hours, these bacteria multiply to the point where they can attach and self-assemble into an adhering continuous film and attach to a surface, which is biofilm. The matrix that hold the bacteria together in a biofilm is normally made from secreted polysaccharides. Bacteria existing in the form of biofilm can be resistant to antibiotics even if the same antibiotic is effective to kill the same bacteria in planktonic form. It is believed that the production of the greatest quantities of mucus or secreted exudate, and the greatest symptoms of the disease, is associated with biofilm. Biofilm can be killed by antibiotics or by drying out. One way a Tympanostomy Tube helps treat otitis media is by providing ventilation that promotes the drying out of the biofilm.

Embodiments of the invention pertain to methods for treating middle ear infections with an antibiotic-releasing ear tubes and devices. The method may comprise the steps: 1) forming a "meniscus" that bridges the ear tube surface and the liquid exudate inside the middle ear, 2) releasing the drug from the tube into the exudate in the middle ear, 3) transporting the released drug in the exudate to the middle ear space (and mucosa) by means of diffusion and convection, and 4) suppressing and killing bacteria (planktonic and biofilm) within the middle ear, thus decreasing inflammation and post tympanostomy tube otorrhea (PTTO).

Each of these steps is defined by parameters necessary to achieve the desired outcome, namely, the effective treatment of middle ear infections using a drug-releasing ear tube. The treatment method includes suppressing Otitis Media by the drug releasing ear tube when the middle ear is filled, or partially filled, with exudate leading to a decrease in the duration and frequency of post-tympanostomy tube otorrhea (PTTO). The antibiotic is released into the exudate due to its solubility in water and to its diffusion into a liquid film near the tympanostomy tube surface (diffusion layer). Transport of the antibiotic from the tube surface into the exudate bulk liquid and into the middle ear mucosal surface by convection then occurs due to either natural or intentional head movement and head reorientation. This in turn leads to the killing of suspended bacteria (planktonic) leading to prevention of biofilm growth on middle ear mucosa. More details of steps of the treatment methods are provided below:

1). Formation of "meniscus or bridge" between ear tube surface and liquid in the middle ear: Meniscus formation on the tympanostomy tube surface (known as capillarity) is a critical step for drug release: 1) there will be no drug release from the tympanostomy tube without meniscus formation, and 2) meniscus geometry determines the diffusion path of antibiotic release to remote middle ear sites.

Figures 2A, 2B:
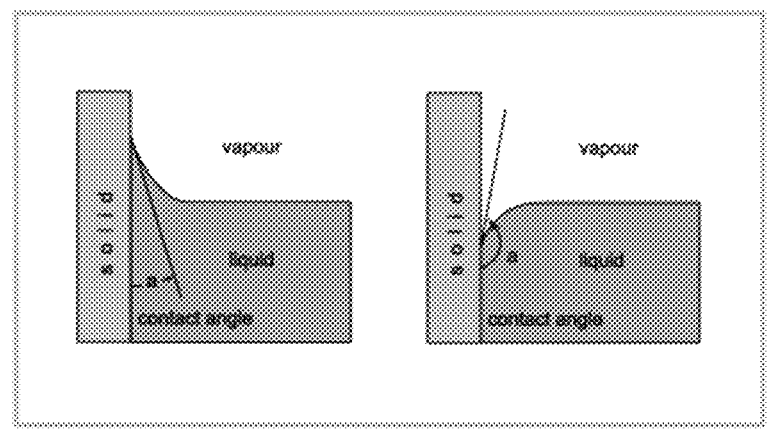
FIG. 2A shows a meniscus for a liquid adjoining a hydrophilic material.
FIG. 2B shows a meniscus for a liquid adjoining a hydrophobic material.

The meniscus at a vertical plate is shown in FIGS. 2A and 2B for hydrophilic and hydrophobic conditions, respectively. The meniscus height is given by:

$$h = a(1 - \cos \theta) \quad (1)$$

where a is the capillary constant which equals 2.8 mm for water and is defined by Equation (2)

$$a = \sqrt{\sigma(\rho g)^{-1}} \quad (2)$$

where $\sigma$=surface tension of the liquid; $\rho$=density of the liquid, and g=the gravitational constant. In order to allow the meniscus to form, the tube needs to be hydrophilic, a condition that is satisfied in our ear tubes and devices.

In embodiments of the invention, the meniscus forms a bridge between the liquid in the middle ear and the tympanostomy tube surface, and allows drug release into the liquid present in the middle ear. It is believed that there is no significant quantity of drug released from the tympanostomy tube when: i) the middle ear is dry (no liquid contacting the implant), ii) there is no inflammation, and iii) the Eustachian tube is functional (patent). According to this method, there is no significant drug release unless there is liquid present in the middle ear. This mechanism avoids drug losses from the tympanostomy tube during the time when there is no infection.

2). Release of drug from the tympanostomy tube to exudate in middle ear—need for convection: If diffusion is the only mechanism for transporting drug from the Tympanostomy Tube to the middle ear, the tranposrt is very slow. According to the Einstein Equation (Equation 3), and assuming a typical drug diffusivity of 10E-6 cm2/sec, it will take 3 hours for the drug to travel only 1 mm.

$$y=\sqrt{Dt} \qquad (3)$$

where y=distance travelled, D=diffusivity, and t=time.

While this is of some usefulness for transporting drug locally, if drug is to reach distant portions of the middle ear, it is desirable that additionally there be some convection (liquid movement) in the middle ear and around the tympanostomy tube.

3). Transport of released drug with exudate to the middle ear space (and mucosa) by means of convection: Gravitational sinking of liquid film can occur due to a change in head orientation, a process that leads to significant transport of liquid and drug. Our calculations estimate that the motion of a liquid film is appreciable and useful for transport of drug even if the liquid film thickness is assumed to have a small value such as 10 microns, and even if the viscosity of the exudate liquid is assumed to be 10 times what it is believed to be in actuality. Such motion of liquid is achievable as a result of either natural motion of the patient's head or instructed motion of the patient's head. Patients who are children generally move frequently during normal activities, and such movement can be expected to distribute drug-laden liquid around the middle ear. Instructed motion is also possible. Achieving effective drug transport has been proven by the animal model testing results as discussed elsewhere herein.

4). Suppressing and killing bacteria: This is achieved by achieving and maintaining an appropriate concentration of drug in the liquid, as described elsewhere herein.

Tympanostomy Tube and Materials

Figure 3:
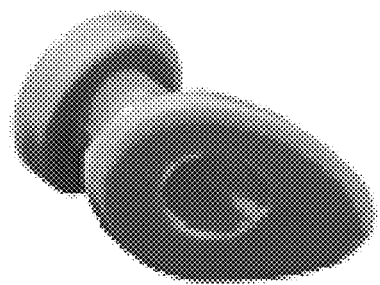
FIG. 3 shows a typical tympanostomy tube that has dissimilar shapes for the two different flanges or enlarged regions.
Figure 4:
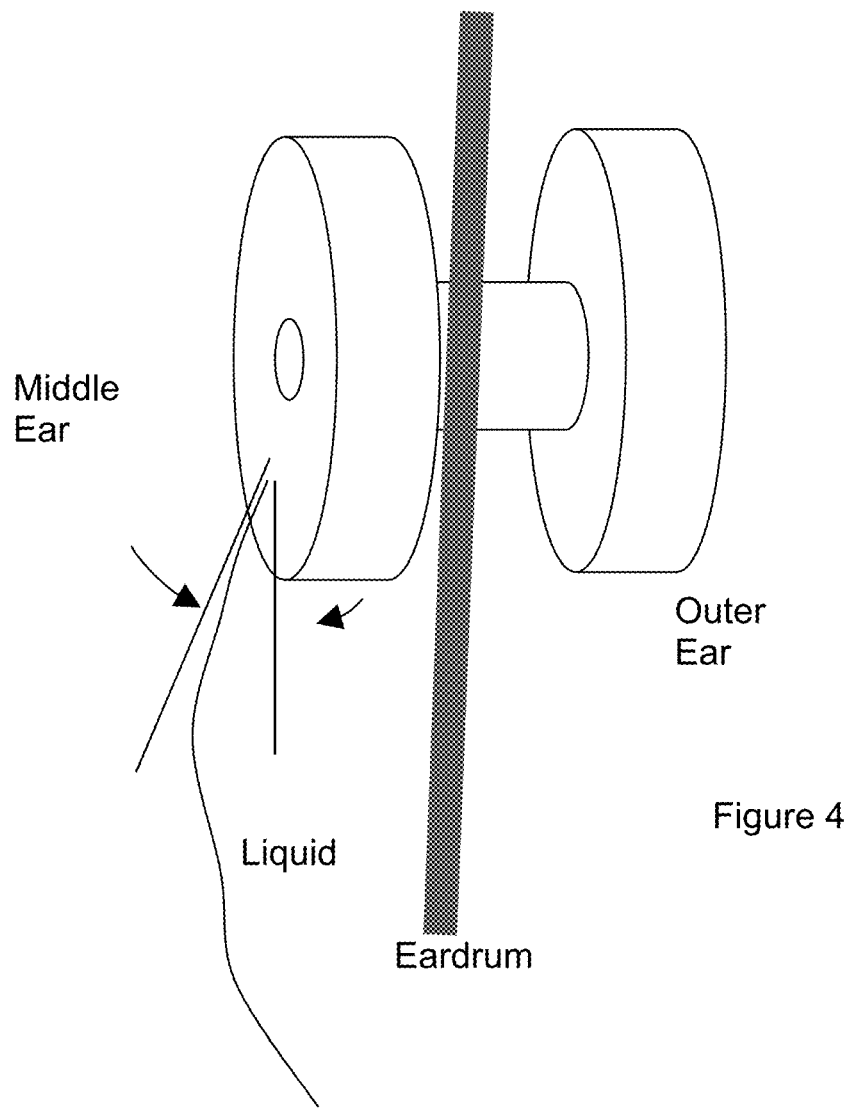
FIG. 4 shows a typical placement of such a tympanostomy tube and the wetting of the tube by liquid in the middle ear cavity.
Figure 5A:
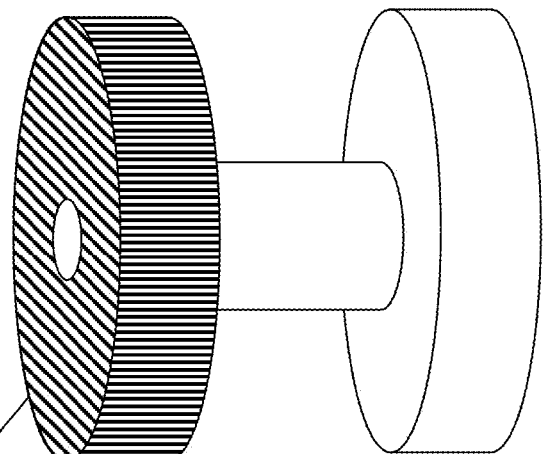
FIGS. 5A through 5E show various enhancements that provide increased surface area on the enlarged portion that is positioned in the middle ear cavity.
Figure 5B:
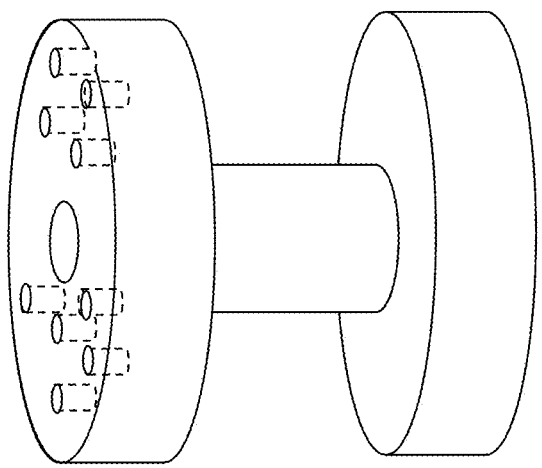
Figure 5C:
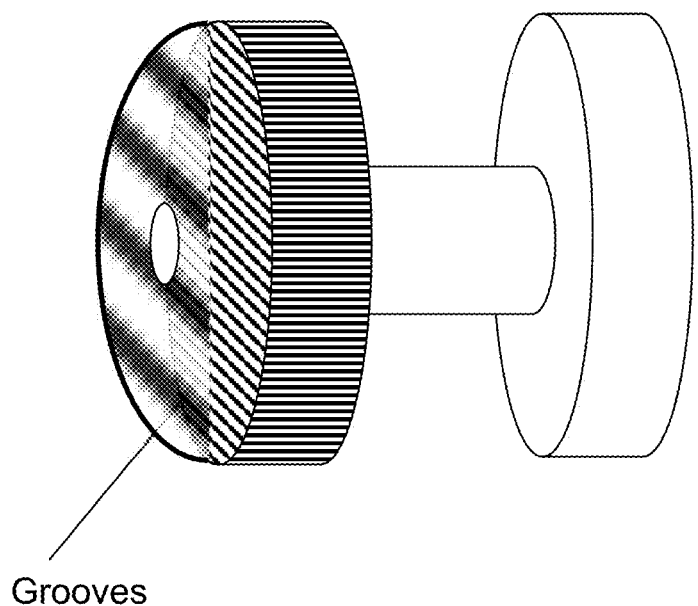
Figure 5D:
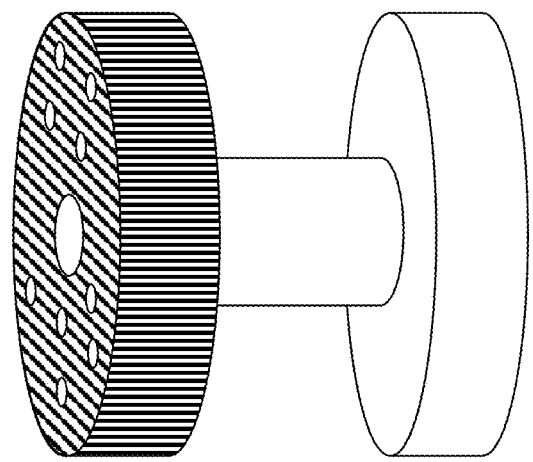
Figure 5E:
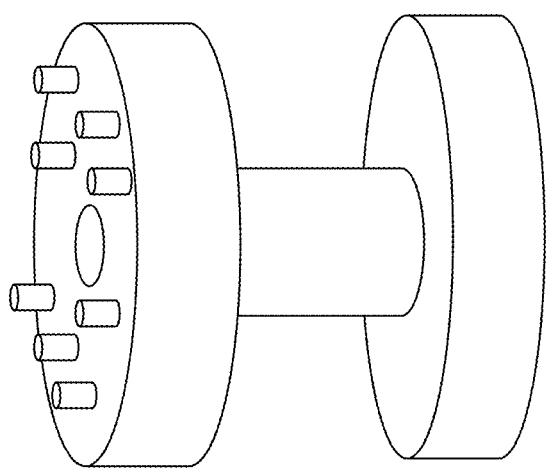

A typical tympanostomy tube is illustrated in FIG. 3. Along a lengthwise direction, in a middle region the tympanostomy tube may have a tubular portion having a hole therethrough. At a first end the tympanostomy tube may have a first enlarged region and at a second end it may have a second enlarged region, with the hole continuing through both enlarged regions. The enlarged regions, which may be referred to as flanges, may be suitable to help the tube maintain its position in the eardrum. The enlarged region that is intended to be outside the eardrum may be generally cylindrical and flat. The enlarged region that is intended to be inside the eardrum may be oriented at an angle other than perpendicular to the lengthwise direction of the tympanostomy tube, and may have a shape that is at least approximately elliptical. The flange may be more pointed at one end that at the opposed end of the approximately elliptical shape. It is also possible for a tympanostomy tube to have only one enlarged region, rather than two enlarged regions as illustrated.

In an embodiment of the invention, there may be provided an implant, such as a tympanostomy tube, that contains a polymeric material that contains an active pharmaceutical ingredient (drug) in a solid form. Examples of such a drug and polymer material combination are described in commonly assigned U.S. Pat. No. 8,747,883. In an embodiment of the invention, the drug and the polymer of which the implant is made are mixed together in the form of a composite or polymeric material. The polymeric material may be such that it can be formed into useful articles such as implants by standard methods of polymer processing such as extrusion, compression or injection molding. For example, the active pharmaceutical ingredient may be such that it is undamaged by heating to temperatures at which the polymer is able to be melt-processed, extruded, compressed or injection molded. At least a component of the polymeric material may be nonresorbable.

The polymeric material may be a blend of more than one polymer. For example, a polymer blend may comprise a non-biodegradable thermoplastic polymer material and a water-soluble polymer material. Examples of non-biodegradable polymer families include: polysilicones, silicones, polyurethanes, polyamides, natural rubber, synthetic elastomers, ethylene-vinyl acetate copolymers, and their blends, and their mixtures.

The non-biodegradable thermoplastic polymer material may itself be a copolymer. For example, it may be ethylene vinyl acetate (EVA). Ethylene vinyl acetate is a copolymer that comprises polyethylene groups and vinyl acetate groups. A natural characteristic of polyethylene alone is hydrophobicity, while a natural characteristic of vinyl acetate alone is hydorophilicity. As discussed elsewhere herein, the proportion of vinyl acetate may be from about 10% to about 50% by weight. The remainder of the copolymer may be polyethylene. Such a proportion results in a copolymer that is hydrophilic. The copolymer may have a melt index less than about 50 g/10 min. as measured by ASTM D1238.

A resorbable polymer could also be used for this portion of the material. Examples of resorbable polymers include poly lactic acid, poly lactic co-glycolic acid, and polycaprolactone.

The water-soluble polymer material may be polyethylene glycol (PEG) having a weight average molecular weight of from about 400 to about 20,000 Daltons. PEG is water soluble, and its solubility may depend on the molecular weight. Even though in the present situation the PEG itself might not leach out from the implant to any significant extent, the presence of such a water-soluble material may increase the ability of active pharmaceutical ingredient to diffuse out of the implant, due to increase in diffusivity and solubility. It is believed, although it is not wished to be limited to this explanation, that this may increase the slope of the second stage of the drug release profile as discussed elsewhere herein. It is also believed that the presence of the PEG increases the hydrophilicity of the surface of the composite material, compared to what the interaction with water would be for the copolymer alone.

The polymeric material may be comprised of a melt blend of: (i) an ethylene-vinyl acetate copolymer (ii) polyethylene glycol, as described. In a melt blend, the components may be intimately mixed with each other. The two described components, in the proportion just described, are completely miscible or dispersed with each other and are capable of forming such a blend. It is believed that in the final product the PEG component does not dissolve out to any great extent, because the two polymers are blended together uniformly on such a small scale, but because the PEG is water-soluble, it makes the composite material more diffusive and more able to release drug to water or hydrated tissues that contacts the implant.

In addition, the polymeric material may be combined with one or more bioactive agents comprising a drug dispersed among the polymer material. The active pharmaceutical ingredient may, in general, be any drug that is thermally stable at temperatures used in processing. Ciprofloxacin is one drug that may be used. Other drugs with different treatment function such as inflammation or cytotoxic cancer targeted agents may also be used to make the polymer materials. The bioactive agents may comprise about 1 to about 60 percent by weight of the total weight of the composite.

The drug may be a member of the fluoroquinolone family of drugs. For example, the drug may be Ciprofloxacin. Although Ciprofloxacin is used for examples, it is believed that other drugs of this same family would work similarly well. In general any antibiotic or drug could be used as long as it is stable at the processing temperatures described herein. The Ciprofloxacin may form a solid solution with the described polymer blend. The solid solution may exist in one or more phases that exist in respective small regions of the implant. There may be a polymer-rich solid solution phase and a drug-rich solid solution phase, in addition to pure drug and pure polymer phases. These two solid-solution phases may form with an interphase boundary between them as the combination of materials is being melted and then cooled down from a processing temperature. In addition, there may be additional discrete Ciprofloxacin existing as small particles embedded within the implant. The discrete Ciprofloxacin particles may be polydisperse having a size distribution, which may be chosen to help achieve desired release characteristics.

Ciprofloxacin itself is available in two chemical forms. There is Ciprofloxacin betaine otherwise known as the free base (which is less soluble in water) and Ciprofloxacin hydrochloride (which is more soluble in water). The Ciprofloxacin may be present in the implant in either form and may be present in the implant in both forms. The use of both forms together, and their relative proportion, may be chosen so as to provide desired solubility and release characteristics. It is also possible to include an anti-inflammatory such as dexamethasone.

The composite material may be melt-processable at a temperature not exceeding 260 C, for example. In an embodiment of the invention, the active pharmaceutical ingredient may be undamaged at such temperature at which the composite is melt-processable.

For a drug such as Ciprofloxacin, some of the drug may exist as a solid solution with the polymeric material, and also some of the drug may exist as solid particles that are discrete with respect to the solid solution. Those particles may have a distribution of particle sizes, which in turn may influence drug release as described elsewhere herein.

The material may be at least moderately hydrophilic with respect to pure water, and may have a contact angle with pure water of 50 degrees or less. This is true for the polymeric material itself and also for the overall material including drug and any other additives.

Amount of Drug Contained in Implant

A drug or active pharmaceutical ingredient contained in an embodiment of the invention can be an antibiotic, an anti-inflammatory, or still other forms of drug, or a combination of any of these.

An example of an antibiotic drug that could be used is ciprofloxacin, in any of its forms. Ciprofloxacin is known to be effective against infections such as middle ear infections (otitis media), and it is known not to be ototoxic. Ciprofloxacin is available in two different forms, Ciprofloxacin betaine (also known as free base) and Ciprofloxacin hydrochloride. Ciprofloxacin betaine has a relatively low solubility in water and aqueous liquids, while Ciprofloxacin hydrochloride has a significantly larger solubility in water and aqueous liquids. Ciprofloxacin betaine form (free base) has a solubility in water, at 20° C., of 79 µg/mL. Ciprofloxacin hydrochloride has a solubility in water, at 20° C., of 30 mg/ml. Even Ciprofloxacin betaine, when in saturated solution in water, has a concentration that is greater than the Minimum Inhibitory Concentration for microorganisms that are of interest in connection with otitis media.

There are several considerations that may pertain to deciding on the amount of drug that may be contained in one of the described implants. There may be a quantity of drug that is a typical desired dosage of drug that is needed, based on medical and physiological considerations, to treat one typical episode of middle ear infection (otitis media). This can be described in part by the quantity Minimum Inhibitory Concentration (MIC) for the organisms being targeted. Other consideration include whether the organisms are present in planktonic or biofilm forms, because the latter will require higher drug consideration during treatment. There may be a second quantity that is a typical amount of drug that is or can be delivered from the implant during the typical course of more than one episode of middle ear infection. Normally it is desirable to treat multiple episodes of OM infections with the same implant. This delivered amount may be based on considerations of the solubility of the drug in water, the solubility and diffusion of the drug in the polymer matrix, the exposed surface area of the implant, the amount of exudate present in the middle ear and its motion within the middle ear region, assumptions about the motion of the liquid within the middle ear, and other such considerations.

In addition to helping to prevent otorrhea or to treat an episode of otitis media during which the device was implanted, after that episode of otitis media, the device still may contain within it a significant remaining amount of drug. This remaining amount of drug may be sufficient to cure or prevent a number of future episodes of the same condition. For example, there may be enough drug in the ear tube to prevent or cure as many as 30 additional episodes of otitis media. Preventing middle ear infection according to the invention may decrease the incidence of post tympanostomy tube otorrhea (PTTO).

In embodiments of the invention, the amount of drug present in the implant may be greater by some factor than the minimum amount of drug needed to treat the course of one episode infection, and may be greater by another factor than the amount that would typically be delivered in treating a typical episode of otitis media. Thus, the amount of drug that is contained in the implant may be sufficient to treat multiple episodes of otitis media, while accounting for the drug losses during the treatment. For example, the amount of drug contained in a tympanostomy tube may be 1000 to 3000 micrograms, depending on the tube geometry, surface area, release kinetics and design.

It can be understood that in embodiments of the invention, the drug that remains in the implant after the first episode of otitis media has run its course may act to catch or diminish subsequent otitis media in their early stages and prevent early-stage otitis media from developing into a full-blown case of the disease. It is believed that after a small amount of fluid has been released due to an early stage of the disease, the drug is released into that fluid and suppresses the release of further fluid and thereby avoids a full-blown infection. It is believed that the released drug from the implant kills planktonic (free-floating) bacteria before they can assemble into a biofilm. Also, in an embodiment of the invention, the continued presence of the drug on the implant itself prevents biofilm from growing on the implant itself and prevents the ear tube from becoming the nidus for subsequent infections.

One reason for why the amount of drug delivered may be greater than the minimum required amount of drug is that there are possible destinations for delivered drug that do not involve direct use in combating infection. These are normally referred to as drug losses. Alternative routes of drug losses of the drug in the middle ear include that drug can be metabolized by enzymes, or can be absorbed in middle ear mucosa and in other bone tissues, or can be drained through the Eustachian tube as a result of being contained in liquid that leaves the middle ear region through the Eustachian tube. It may be difficult to know, for a particular clinical situation, how much of the delivered drug is actually used to treat infection, as opposed to being lost to other mechanisms, especially the unpredictable possible destination of drainage through the Eustachian tube. Accordingly, the delivered amount of drug may be greater than the desired dosage of the drug, or at least roughly equal to the desired dosage of the drug. It is believed that it is not harmful if drug is delivered in a concentration greater than the MIC, especially because the drug is delivered locally rather than systemically. In this case systemic toxicity is expected to be low.

There can be a total amount of the drug that is contained in the implant, or more specifically, contained in that portion of the implant whose surface is able to be contacted by middle ear exudate during typical conditions of infection. A typical tympanostomy tube has the geometry of a hollow tube, having a hole extending along the length thereof, and having an enlargement at either end, which may be called a flange. It may be approximated that the portion of the implant that becomes exposed to exudate in a way that permits drug release to middle ear fluid is the flange and the portion of the tube of the implant that is inside, i.e. on the middle ear side of, the tympanic membrane.

The solid material of which the tube is made can contain 20% ciprofloxacin. This contrasts with a commercial liquid product (Alcon) containing particles of ciprofloxacin in suspension, and which has a ciprofloxacin concentration of 0.3%.

It is further possible that during healthy conditions, when there is essentially no free liquid present in the middle ear, the drug is essentially not released from the implant, because much of the tympanostomy tube does not directly contact liquid that can carry the drug to middle ear mucosa, other parts of the middle ear. Thus, in an embodiment of the invention, the drug in the implant may serve as sort of a reservoir of the drug, such that the drug is released mainly when the patient is experiencing inflammation at the start of an infection or already is suffering from infection. On the other hand, when the tympanostomy tube is not wet, the drug remains within the composite material of which the tympanostomy tube is made.

It is believed, although it is not wished to be limited to this explanation, that if drug has been depleted from the exposed surface of the enlarged region that is inside the middle ear cavity during treatment of an episode of otitis media, then during a subsequent period of time there may be diffusion of drug from other parts of the tympanostomy tube that acts to replenish the drug near that exposed surface.

In an embodiment of the invention, the two forms of Ciprofloxacin can be combined in a single implant so as to achieve a desired the rate of delivery, the solubility limit of the drug in middle ear exudate or release of the drug. A higher proportion of Ciprofloxacin hydrochloride will result in faster release, while a higher proportion of Ciprofloxacin betaine will result in slower release. Also, use of a higher proportion of Ciprofloxacin hydrochloride will increase the saturation concentration of Ciprofloxacin in the middle ear fluid or the ability of the drug to dissolve easily into the liquid, thereby helping to achieve at least the Minimum Inhibitory Concentration and helping to kill bacteria. The Minimum Inhibitory Concentration is the smallest concentration of a drug in water that will inhibit growth of a particular bacteria in solution.

The saturation concentration of ciprofloxacin from the device of embodiments of the invention, in water that has contacted the implant, can be compared to the Minimum Inhibitory Concentration for organisms that cause otitis media. The MIC for certain organisms is given elsewhere herein. It may be desirable that the concentration of the drug in the liquid of the middle ear be 10 times to 100 times the MIC. The volume of the middle ear cavity is approximately 1 cubic centimeter. It may be assumed that the middle ear cavity is half full with liquid, especially in the case of a patient who already has a tympanostomy tube implanted. On the other hand, it can be assumed that over the course of a disease episode the liquid changes once, so that twice that amount of liquid needs to be brought to the desired concentration of drug. So, in essence, the amount of liquid to be brought to the desired drug concentration (which is 10× to 100×MIC) is nominally 1 cubic centimeter.

The quantity Minimum Inhibitory Concentration (MIC) is the smallest concentration of a drug in water that will inhibit growth of a particular organism. It may be desirable for the administered concentration of a drug to be some multiple of this quantity. MIC for Ciprofloxacin is given here for several organisms typical of otitis media. For *Pseudomonas aeruginosa*, the MIC is 0.09 micrograms per milliliter. For *Staphylococcus aureus* GFP, the MIC is 0.28 micrograms per milliliter. For *Staphylococcus aureus* LUX, the MIC is 0.28 micrograms per milliliter. For *Haemophilus influenza*, the MIC is 0.06 micrograms per milliliter. For *Streptococcus pneumonia*, the MIC is 0.75 micrograms per milliliter.

The MIC for various strains of bacteria, which are 0.09 micrograms per milliliter (for *Pseudomonas aeruginosa*); 0.28 micrograms per milliliter (for *Staphylococcus aureus* GFP); 0.28 micrograms per milliliter (for *Staphylococcus aureus* LUX); 0.06 micrograms per milliliter (for *Haemophilus influenza*); 0.75 micrograms per milliliter (for *Streptococcus pneumonia*); can be compared to the saturations solubilities of the two forms of ciprofloxacin in water.

Ciprofloxacin betaine (free base) has a solubility in water, at 20° C., of 79 µg/mL. Ciprofloxacin hydrochloride has a solubility in water, at 20° C., of 30 mg/ml. So, the saturation concentration of Ciprlfloxacin betaine in water is already larger than the MIC for all of these microorganisms, by a useful margin. However, if still further margin is desired, in embodiments of the invention, it is possible to provide some of the ciprofloxacin in the implant in the form of ciprofloxacin betaine and to provide the rest of the ciprofloxacin in the form of the more-soluble ciprofloxacin hydrochloride. The relative proportion of the two kinds of Ciprofloxacin can be chosen so as to provide a saturation concentration that is a desired multiple times the Minimum Inhibitory Concentration for the most difficult-to-kill organism. Typically, more than 2 to 20 micrograms/milliliter of Ciprofloxacin is needed to achieve effective treatment. This concentration may have to be increased by a factor of 5 to 10 for the cases when the middle ear mucosa are covered by biofilm. So, in such a worst-case scenario, it may be desirable to have a ciprofloxacin concentration that is slightly greater than the saturation concentration of ciprofloxacin betaine. These calculations can be used to calculate the total amount of drug that may need to be contained in the tympanostomy tube so as to be able to treat a desired number of episodes of otitis media or similarly prophylactic action against early-stage otitis media.

It is possible that the tympanostomy tube may contain a large enough quantity of drug so that over the course of time of treating a particular patient, not all of the drug that is contained in the tympanostomy tube will be released or will be needed. Of course, it is beneficial that the drug is available if needed. Over the course of time, it is typical that the tympanostomy tube will eventually be pushed out of the eardrum and the eardrum will heal. When the tympanostomy tube is pushed out of the eardrum, it usually falls into the outer ear and then out of the patient's body. This may happen a year or so after placement of the tympanostomy tube. Similarly, for other implants in other mucosal cavities, there can be an amount of drug held in reserve for possible future use, with release when the implant is exposed to aqueous liquid.

It can be understood that when tube is implanted, it becomes an effective treatment against bacteria of new infections at the stage when the bacteria are planktonic during early stage, which is the stage at which the antibiotic is most effective against the bacteria. So, the probability bacteria progressing to the stage of biofilm formation becomes low.

Liquid-Air-Solid Boundary, and Transport Mechanisms

In an embodiment of the invention, advantage may be taken of the fact that, in a patient who has an early stage of middle ear infection that causes inflammation of the mucosa, the middle ear region generally becomes partially full of secreted liquid exudate but is not completely full of liquid exudate. This means that there is a liquid-air interface, and in fact at the surface of the middle ear tissue there is a triple interface of solid and liquid and air. As already mentioned, in the same patient when in a healthy condition, the middle ear region would have essentially no observable liquid, other than the tissue surfaces perhaps being moist in equilibrium with the relative humidity inside this mucosal cavity.

In an embodiment of the invention, the physical properties of the drug-containing implant may be chosen such that the surface of the implant is wettable by water or typical exudate liquid, having a contact angle of less than 50 degrees and preferably close to zero. For example, the polymeric material described elsewhere herein, which is a blend of ethylene vinyl acetate and polyethylene glycol, showed good wetting with water and had a contact angle between 0 degrees and 70 degrees.

In embodiments of the invention, the release of the drug may be triggered or enabled by the presence of liquid contacting the surface of the implant. Even more, as described elsewhere herein, the transfer of drug from the implant to the liquid in the middle ear can be enabled by the successive wetting of the surface of the implant by liquid followed by de-wetting, with that process being repeated in succession.

The body cavity can contain air under at least some conditions and can contain at least some liquid under at least some other conditions.

One mechanism of drug transport is diffusion. This can include diffusion through solid polymer, and diffusion through adjacent liquid, which may be stagnant liquid. It is also necessary, for release of the drug, that there be a dissolution step in which the drug at the surface of the implant dissolves into a liquid. It can be appreciated that drug release that responds to the presence of liquid provides opportunities for controlling, in useful ways, when drug is released or is not released. In embodiments of the invention, there may be only a limited amount of surface area of the implant that is in contact with any tissue during healthy conditions in which there is essentially no explicit liquid. However, there may be other surface area of the implant that becomes contacted by liquid when there is liquid exudates present during infection, and especially at the beginning of infection where this inflammation of the mucosal cavity and associated tissues.

Enhanced Surface Area

It can be appreciated that some steps involved in drug release may be a function of the amount of surface area of the implant. This may be true, for example, for mass transfer processes such as dissolution, i.e., dissolution of drug into the liquid, that occur at the interface between the implant and the liquid. In an embodiment of the invention, the implant may be provided with a surface that has an enhanced amount of surface area compared to what the surface area would be if the surface were smooth. For example, the surface may be provided with grooves, ridges, roughness, protrusions, recesses, holes, texturing, or any other form of irregularity. Roughness may be in the range of about 2 to 250 microinches root-mean-square. Such enhanced surface area may be provided on the portion of the tympanostomy tube that is intended to reside in the middle ear region, such as the flange or enlarged region. Such enhanced surface may be provided on generally any surfaces of the flange that are intended to be located inside the middle ear region, such as exposed surface, circumferential surface, and opposed surface. Such enhanced surface may also be provided anywhere else on the implant as may be desired, or on the entire implant.

The details of the surface on the end of the tympanostomy tube which is intended to be located in the outer ear outside the eardrum, are believed to be of less importance for the treatment of otitis media. Such surface enhancement features could also be manufactured into that end of the implant, or generally anywhere on the implant, but they do not have to be so manufactured. For example, the tympanostomy tube may have outer flanges that have smooth surfaces. The flange may have a thickness H along an axial direction of the tympanostomy tube, and the flange may have an outside diameter of DF.

In current tympanostomy tubes, some features may be axisymmetric, which means that they have an axis of rotational symmetry such that for any positioning of angular orientation around the axis of symmetry, the tube appears the same. That axis usually corresponds to the lengthwise hole of the tube. In embodiments of the invention, it is possible that the overall geometry of the tympanostomy tube may be axisymmetric, but the surface enhancement features, or at least some of the surface enhancement features, might be nonaxisymmetric. For example, grooves that are parallel to each other might make the device nonaxisymmetric. Such a feature could provide performance advantages with respect to influencing the motion of liquid on or near the implant; on the other hand, such would require implantation of the device in a specific orientation. Of course, it also is possible that a device could be provided with surface enhancement features that are themselves axisymmetric and would not violate the axisymmetry of the overall shape of the device. For example, grooves on the face of the flange could be concentric with each other like the circles on a target.

A tympanostomy tube having a central tube having a long direction having a central hole along said long direction having a hole diameter DH, and having an outside diameter DT, and having a generally cylindrical flange attached to the central tube, wherein the flange has a thickness H along said long direction of said central tube, and has a maximum outside diameter DF. In this case, the smooth exposed surface area of the flange would be pi*DF*H+0.25*pi*(DF^2−DH^2)+0.25*pi*(DF^2−DT^2). The enhanced-surface flange may have a surface area that is greater than this quantity. In general, the implant may have an enveloping surface area of an enveloping surface, and it may have an actual surface area of the enhanced surface. The actual surface area may be greater than the enveloping surface area. For example, the actual surface area may be as much as 30% greater than the enveloping surface area, or 50% greater, or it may even be double the enveloping surface area.

It is further possible that the presence of grooves or certain other features may create a wicking effect, which may draw liquid into the grooves. This may enhance the ability of the device to wet and to attract or retain liquid within the grooves or similar feature due to surface tension.

For an embodiment of the invention, that is intended to be placed in a mucosal cavity other than the ear, enhanced surface features may be located appropriately with regard to the expected contact of the device with bodily liquids in a particular application. For example, the location or even the orientation of the grooves or other features may depend on which regions of the device are expected to be wetted by bodily fluids.

Still further, it is possible for a device to have a circumferential surface on which are produced axially-oriented grooves. Such grooves would technically make an otherwise axisymmetric device non-axisymmetric, but the grooves could occur at a uniform spacing making the device periodic in the sense of the existence of positions in which the device is indistinguishable from other rotational positions in which it could be placed. In such a situation, there might be so many possible angular orientations that are indistinguishable from each other that there would be no significant constraint on the surgeon as far as angular orientation of the device when it is placed in the patient.

Enhanced Mass or Volume

In an embodiment of the invention, it is possible that the tympanostomy tube could be dimensioned or designed in certain ways so as to occupy more volume than would otherwise be required, so that it thereby contains an increased quantity of drug. For example, referring now to FIG. 6, the portion of the implant that is intended to be placed outside the eardrum, in the ear canal, could be more massive than would otherwise be required. For example, the flange or enlarged portion hat is intended to be placed outside the eardrum, in the ear canal, could be longer along the lengthwise direction of the implant than would otherwise be required. This is illustrated in FIG. 6A, showing the tympanostomy tube in isolation, and FIG. 6B, showing the tympanostomy tube in place in the anatomy of the ear.

Figure 6A:
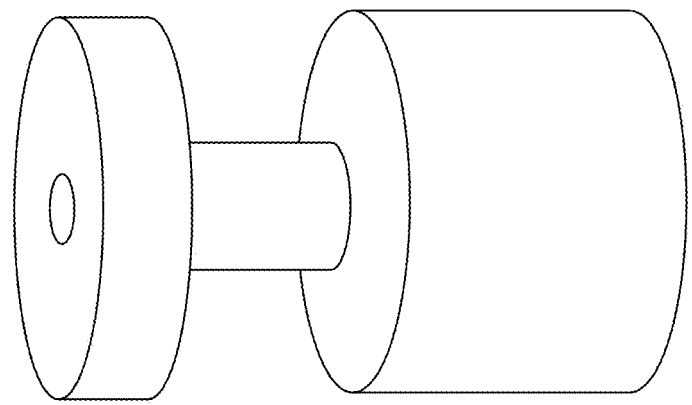
FIG. 6A shows an enhancement that provides increased mass or volume of the portion of the tympanostomy tube that is located in the ear canal.
Figure 6B:
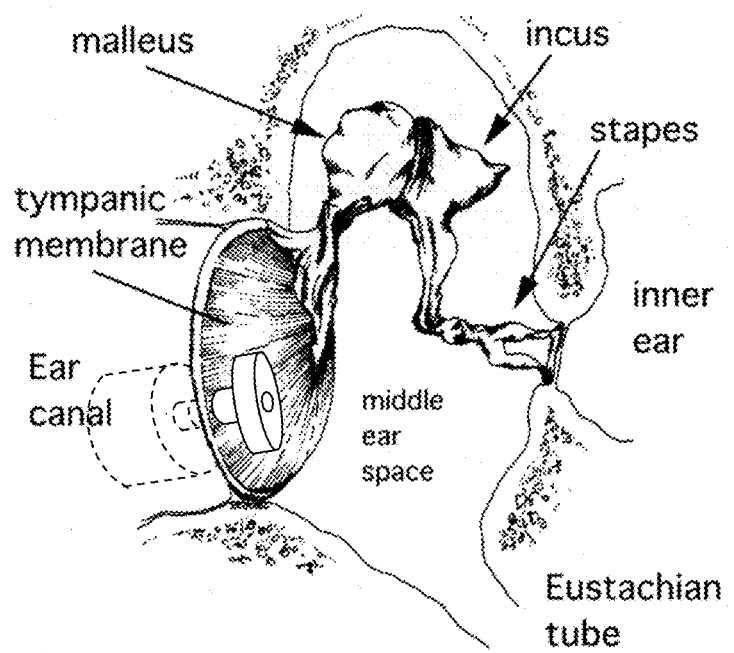
FIG. 6B shows the placement of such a tympanostomy tube in the anatomy of the ear.
Figure 7:
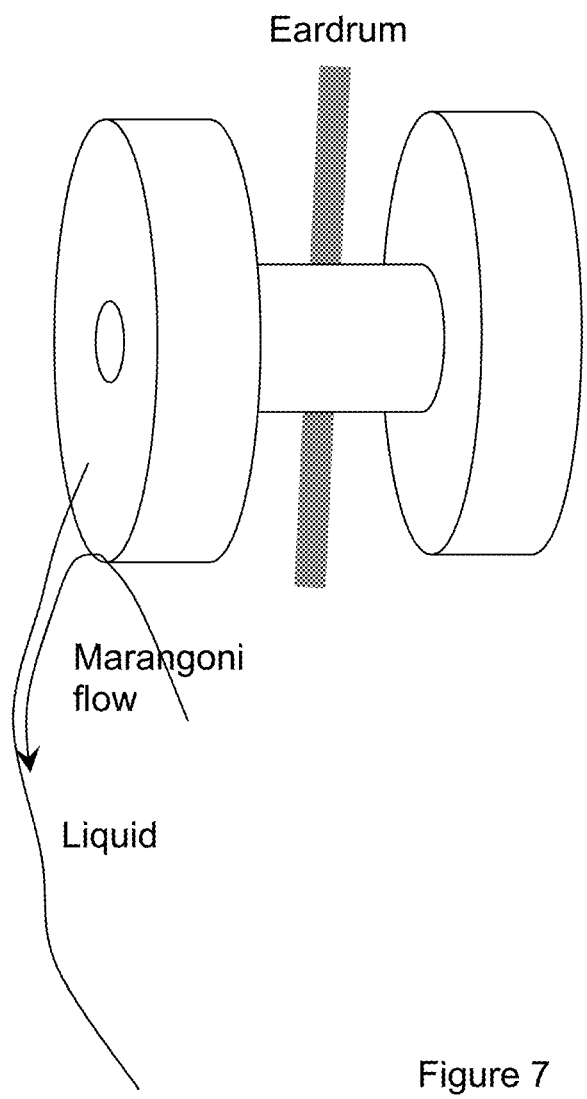
FIG. 7 shows possible motion of liquid in a middle ear cavity under the influence of the Marangoni effect.

For example, as illustrated in FIGS. 6A and 6B, the flange that is intended to be placed in the outer ear could have twice as much mass as the flange that is intended to be placed inside the middle ear cavity, or the flange that is intended to be placed in the outer ear could have more than twice as much solid volume as the flange that is intended to be placed in the middle ear. The outer flange may contain more than half of the mass of the tympanostomy tube, or more than two-thirds of the mass of the tympanostomy tube. The outer flange may contain more than half of the drug content of the tympanostomy tube, or more than two-thirds of the drug content of the tympanostomy tube.

It can be appreciated that even though drug located in a feature such as the outer flange is initially located outside of the middle ear, drug in such a location can migrate by diffusion within the implant so that it reaches the inner flange or enlarged region and becomes available for release into the middle ear cavity.

It can be appreciated that for the process of drug diffusing from the outer flange to the inner flange, the narrow tubular portion of the implant that passes through the tympanic membrane is a region of resistance (literally a bottleneck) for such mass transfer. Accordingly, materials choices are available to increase the effective diffusivity of the materials. First, with the combination of materials described herein, such migration is especially possible at times when the implant is moist. Second, in embodiments of the invention, especially with an enlarged outer mass, the composite may be porous. Such porosity may increase the diffusivity of the composite material and may make it easier for drug that is stored in the outer flange to travel to the inner flange, where the drug may be released to the liquid of the middle ear. The porosity of the tympanostomy tube can provide a place for liquid or moisture to reside and improve the diffusion of drug within the tympanostomy tube. However, it is not necessary for the implant to be porous, and it is possible that the implant be non-porous.

In addition, in embodiments of the invention, certain dimensional choices can be made to improve the diffusion of drug through the central tubular region. it may be provided that the first flange has a minimum separation distance from the second flange that is no more than three times the thickness of the tympanic membrane, or no more than two times the thickness of the tympanic membrane. A typical thickness of the tympanic membrane is 0.1 millimeter. On this basis, the minimum separation distance between the flanges may be no more than 0.3 mm, or may be no more than 0.5 mm. Of course, it is also possible to make the outside diameter of the central tube as large as possible, and the inside diameter of the central tube as small as possible. It is also possible to choose the outside diameter of the central tube to be somewhat large, within the dimensional constraints inherent in the anatomy, and for the inside diameter of the hole or passageway to be somewhat small, consistent with the requirement for the hole to provide passage of either gas or liquid in appropriate circumstances. For example, there may be provided a cross-sectional area of the solid material of the wall of the central tube, having an area of at least 1.4 mm$^2$.

Presence of Surfactant

In an embodiment of the invention, the implant may be a composite containing, in addition to the described polymer and active pharmaceutical ingredient as described herein, an additional component that is a surfactant. In an embodiment of the invention, the drug and the polymer and the surfactant may be mixed together in the form of a composite. The composite may be such that it can be formed into useful articles such as implants by standard methods of polymer processing such as extrusion, compression or injection molding. For example, the composite may be melt-processable at a temperature not exceeding 260 C. For example, the active pharmaceutical ingredient and the surfactant may be such that they are undamaged by heating to temperatures at which the polymer is able to be melt-processed, extruded, compressed or injection molded. For example, the active pharmaceutical ingredient and the surfactant may be such that they are undamaged by heating to a temperature of 260 C.

It can be noted that the described surfactant is part of the implant and will exist in that portion of the implant that is inside the eardrum, and will contact fluid in the middle ear. This is not the use of surfactant as a way of increasing diffusion of the drugs etc. through the intact eardrum.

Many surfactants are possible. The surfactant may be chosen such that it is not ototoxic. A suitable non-ototoxic surfactant can be chosen from among the classes anionic surfactants, cationic surfactants, and nonionic surfactants. An example of an anionic surfactant is sodium dodecyl sulfate (sodium lauryl sulfate). An example of a suitable cationic surfactant is benzalkonium chloride. Examples of suitable nonionic surfactants include: poloxamers such as poloxamer 407; pluronics such as pluronic 68 and pluronic 168; polysorbate, such as polysorbate 20 to polysorbate 80; pyloxapol.

The surfactant may be such that when it leaches out of the implant into the liquid, it lowers the surface tension of the exudate or other liquid to a value in the range of less than 60 dynes/cm to about 40 dynes/cm so that the exudate or other liquid wets the surface of the implant more easily than would be the case in the absence of the surfactant.

Here is described one possible mechanism of operation, although it is not the only possible mechanism of operation and it is not wished to be limited to this mechanism. A drop of liquid, such as a drop of liquid formed because of inflammation due to bacteria, may form near the Tympanostomy Tube, and may contact the Tympanostomy Tube. Such contact may occur because the droplet is growing due to inflammation, or due to motion, or due to any other reason. The droplet may wet the Tympanostomy Tube and may dissolve some surfactant. The surfactant may be such that it that when the surface of the implant is exposed to liquid, the surfactant leaches out from the implant into the liquid of the middle ear or other body cavity. The liquid may have its surface tension reduced as a result of dissolving the surfactant. This reduced surface tension may result in a shallower contact angle of that drop of liquid with everything that it touches including the tissue. This reduced surface tension may result in the drop spreading out because of lower contact angle. This spreading may in turn result in the droplet contacting still other drops, and generally can help establish a more continuous film of liquid, which is advantageous in transporting drug around the middle ear cavity.

Marangoni Effect

Further in regard to surface tension, it is useful to understand the Marangoni effect. The Marangoni effect describes the situation where different parts of a liquid have different surface tension, otherwise referred to as a gradient in surface tension.

In embodiments of the invention, in which surfactant is included in the material of the implant, the liquid that contacts the implant and receives surfactant by dissolving it from the implant, has a lower surface tension of than liquid in other parts of the middle ear. The unequal surface tension or the surface tension gradient causes a movement of liquid. At the surface of the liquid, liquid will move away from the surfactant source along the surface of the liquid, from the region of low surface tension to the region of high surface tension. This will transport antibiotic-containing liquid away from the implant to other parts of the middle ear, by convection. In order to replace the liquid that flowed away along the surface, it is possible that other liquid will flow in at places that are not a free surface, in order to replace the liquid that moved away along the free surface. However, after this has happened to a certain extent, there may be some equalization of surface tension among places in the liquid in the middle ear. Thus, the Marangoni effect may be most prominent when liquid first contacts the implant after a period of no liquid presence or dryness. So, the Marangoni effect may be somewhat transient or temporary. Continued existence of the Marangoni effect would depend on surfactant being removed from the liquid through metabolism or other means, or on the existence of conditions that cause surface tension gradient such as dilutions caused by more exudate secretions.

Porosity

In an embodiment of the invention, the tympanostomy tube, or more generally the implant, or portions thereof, can be porous and can have a porosity fraction. Porosity can be achieved by molding particles of a pore-forming substance such as a water-soluble substance, together with all of the other described substances, and then leaching out the pore-forming substance in a later step.

For example, the pore-forming substance or porogen can be water-soluble. For example, the porogen can be any one or more of various sugars. Different sugars have different solubilities in water. Polyethylene glycol could similarly be used as a porogen. Different molecular weights of PEG have different solubilities in water. Another possible porogen is polyethylene oxide. It is even possible to use a low molecular weight polyethylene glycol (such as a molecular weight of about 400 Daltons) as the porogen at the same time as the polymeric material also contains a higher molecular weight, less-water-soluble form of polyethylene glycol (such as a molecular weight of 10,000 to 15,000 Daltons) as a component of a blend that is the polymeric material. The higher the fraction of porogen in the as-molded version of the product, the greater the increase in diffusivity can be expected to be after the porogen has been leached out. The fraction of porogen in the as-molded product could be in the range of 20% to 50%, which would also be the pore fraction or porosity of the product after leaching out of the porogen. The pores, or at least some of them, could be interconnected. It is believed that interconnectedness can be achieved with the described porogen fraction.

Alternatively, it is also possible that the implant could be non-porous.

Geometry of Liquid Presence

In embodiments of the invention, the release of the drug may be triggered or enabled by the presence of liquid contacting the surface of the implant. Even more, as described elsewhere herein, the transfer of drug can be enabled by the successive wetting of the surface of the implant by liquid followed by de-wetting, with that process being repeated in succession.

The body cavity can contain air under at least some conditions and can contain at least some liquid under at least some other conditions.

Figures 8A, 8B, 8C:
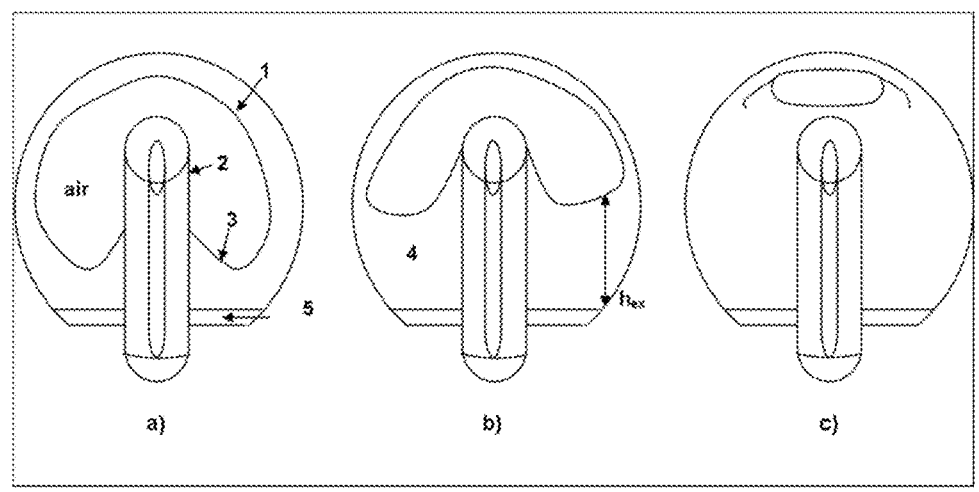
FIGS. 8A, 8B and 8C show various possible situations of the middle ear cavity and amounts of liquid contained therein.

It can be appreciated that the amount of liquid that is present in the middle ear during an episode of otitis media is variable and unpredictable. Also, the properties of the liquid, such as the viscosity of the liquid, are not necessarily known. Another factor relating to unpredictability is that the ability of the Eustachian tubes to drain fluid from the middle ear is variable. This ability may be influenced by such factors as whether or not the adenoid gland is swollen, because a swollen adenoid gland would tend to squeeze the Eustachian tube closed. Thus, there is no single model that would describe every possible physical situation. Several possibilities are shown schematically in FIGS. 8A, 8B and 8C. For these Figures, the orientation of the patient would be such that the patient would be lying on his or her side with the affected ear facing downward. The eardrum is shown in cross-section near the bottom of each illustration. FIG. 8A shows a cross-section of a middle ear cavity having only enough liquid to create a film of liquid on most of the interior surfaces of the middle ear cavity. Such a film would have some mobility due to, for example, changes of orientation of the gravity vector, but might not provide a large amount of convective transfer of liquid. In a situation like this, surface tension effects could be more significant than in the situations of FIGS. 8B and 8C. FIG. 8B shows the middle ear cavity partially full of liquid, in a situation that would provide quite easy motion of liquid. FIG. 8C shows a middle ear cavity that is almost completely full of liquid, which might not be an optimal situation for creating convective fluid motion by reorientation of the head. These figures illustrate that the thickness of the liquid film, or the amount of fluid present, may influence how much motion of fluid may result from changes in orientation with respect to gravity, from dynamic motion, and from surface tension effects, and from any other mechanism.

In some instances, with reference to a head orientation that is upright, it is possible that if the liquid level in the middle ear reaches the level of the hole in the tympanostomy tube, then excess liquid will drain out of the middle ear through the tympanostomy tube and then out through the ear canal (outer ear). This is normally called otorrhea. It is also possible that, with a slightly smaller amount of fluid in the middle ear, the fluid may form a thin liquid layer or film on the surface of tissues. Such liquid may be exuded from the tissues. The mechanics of liquid film movement over a surface is always complicated as well.

There are several ways that the property of surface tension can be manipulated in order to achieve desired results.

First of all, as discussed elsewhere herein, the polymer material itself can be formulated so that it is hydrophilic and easily wettable by liquid in the middle ear. As discussed elsewhere herein, the relative proportion of copolymer components in EVA (ethylene vinyl acetate) influences the wettability of that copolymer, and the presence of PEG (poly ethylene glycol) in the blend influences the wettability of the composite material.

The Marangoni effect, as discussed herein, can cause motion of liquid in situations that exhibit spatial variations of surface tension, such as where new liquid appears arising from inflammation, or where liquid contacts the tympanostomy tube and thereby receives surfactant.

Convection, i.e., motion of liquid in the middle ear

In embodiments of the invention, during healthy conditions, there may be only a limited amount of surface area of the implant that is in contact with any tissue, and there may be essentially no explicit liquid in the middle ear region. In embodiments of the invention, it is necessary, for release of the drug, that there be a dissolution step in which the drug at the surface of the implant dissolves into a liquid. It can be appreciated that drug release that responds to the presence of liquid provides opportunities for controlling, in useful ways, when drug is released or is not released.

When inflammation is present, liquid is generated in some amount, which may vary according to the conditions of the inflammation. In this situation, surface area of the implant that becomes contacted by liquid when there is liquid exudate present during inflammation. There can be some diffusion of drug through the liquid, but not enough to be significant for the time scales and dimensions involved.

A physical mechanism that can influence the position and motion of liquid in a region that is partially filled with liquid is gravity. As a transport mechanism, it can be thought, although it is not wished to be limited to this explanation, that delivery and transport of the drug in the middle ear is aided by motion of liquid that contains the drug. It can further be appreciated that what is useful for transport and delivery of drug is not simply the presence of liquid in contact with the drug-bearing implant. Instead, or in addition, there can be the motion of that liquid from one place to another within the middle ear or other mucosal cavity. Such motion of liquid can physically move drug from one place to another, such as from the source of the drug at the implant to a destination in the form of various tissue surfaces within the middle ear cavity. Also, it is possible that motion of the liquid can produce sequential or repetitive wetting and de-wetting of the drug-containing surfaces of the implant that are exposed to the environment of the middle ear or other mucosal cavity. Such wetting and de-wetting can replace the liquid immediately contacting the surface of the implant with fresh liquid, which may avoid having the liquid immediately at the surface become saturated with dissolved drug and may thereby improve the mass transfer of drug out of the implant.

For example, there can be envisioned a sequence of events in which liquid travels to the implant, remains in contact with the implant for a sufficient time to receive drug from the implant, travels away from the implant, contacts tissues in need of drug and delivers the drug to those tissues, and after becoming depleted of the drug, returns to the implant to receive more drug. The cycle can be repeated for repeated motions of the liquid. Such a cycle can transport drug more effectively than is possible in a completely stationary system even if such a system contains liquid in a stationary state.

Referring now to FIG. 10A and FIG. 10B, there are shown a schematic illustrations of how a thin liquid film can move around the middle ear cavity as a function of body position. FIG. 10A shows steady-state positions and views of position of the liquid film. FIG. 10B shows a time history of bodily positions and shows positions of a liquid film upon initial assumption of a bodily position as well as after a bodily position has been occupied for enough time to allow the film to reach a final configuration. In FIG. 10B, hatched regions of the surface indicated regions that have been wetted due to the illustrated motions that occurred previously.

This bulk motion of liquid in the middle ear can be aided by motion of the patient's body in either of two ways: random motion and instructed motion.

Random Motion, Motion from Everyday Activities

A patient, even a patient who is feeling sick, is likely to make some number of body movements during normal activities when awake, and even a certain number of movements during sleep.

Some proportion of these bodily movements will involve head motion. It is possible that such movements will cause fluid in the middle ear to move in response thereto. If drug leaches out of the implant into the fluid, such motion of fluid can be expected to accomplish two beneficial effects: it may physically transport drug from its source to places within the mucosal cavity that are in need of it; and it can refresh the fluid that is in immediate contact with the implant, replacing fluid that may have become saturated or nearly saturated with drug, with fluid that has a lower concentration of drug, so as to enhance further dissolution of drug from the implant. This can be analogous to stirring to cause dissolution of a powder in any ordinary situation.

It can be expected that random motions of the patient's head during activities of daily life will accomplish some of this fluid motion. In addition, it can be expected that for otitis media, the population of patients is likely to be young children, such as children three years old or younger. For such children, it might be difficult to have them move their heads in instructed positions and sequences of positions, but there may be an abundance of head motion from ordinary activities. Such motion may still be beneficial for aiding in the transport of drug from the implant to regions of the middle ear.

Instructed Motion

One way of causing such fluid motion is by using gravity to aid in the transport and delivery of drug. This can be done by appropriately orienting and changing the orientation of the part of the patient's body where the implant is located. It can be appreciated that temporal variations in the position of the liquid in the patient's body cavity such as the middle ear can be used to move liquid and thereby move drug around the body cavity of interest as just described. This is true in part because of the presence of some air in the body cavity of interest.

FIG. 11E shows an instructed bodily movement of rotating the head around the spinal axis. FIG. 11F shows an instructed set of bodily positions involving leaning leftward and rightward, from an upright position. FIG. 11G shows an instructed set of bodily positions involving lying down in various orientations.

Orientation of the patient's head reorientation to the left and to the right leads to liquid movement and to strong convection, as shown in FIGS. 10A and 10B. During the time between head movements, the liquid sinks to the local lowest point due to gravity, thus resulting in additional convection. Since the liquid is always bridged with the ear tube through the meniscus, three processes are expected: 1) mixing middle ear liquid with the released antibiotic, 2) moving the antibiotic liquid mixture to other regions of the middle ear, and 3) further enhancing the release of antibiotics from the tympanostomy tube. Our computations show that release is enhanced as a function of the period of time between head reorientations. More frequent head reorientations lead to more release enhancements.

Figure 11A:
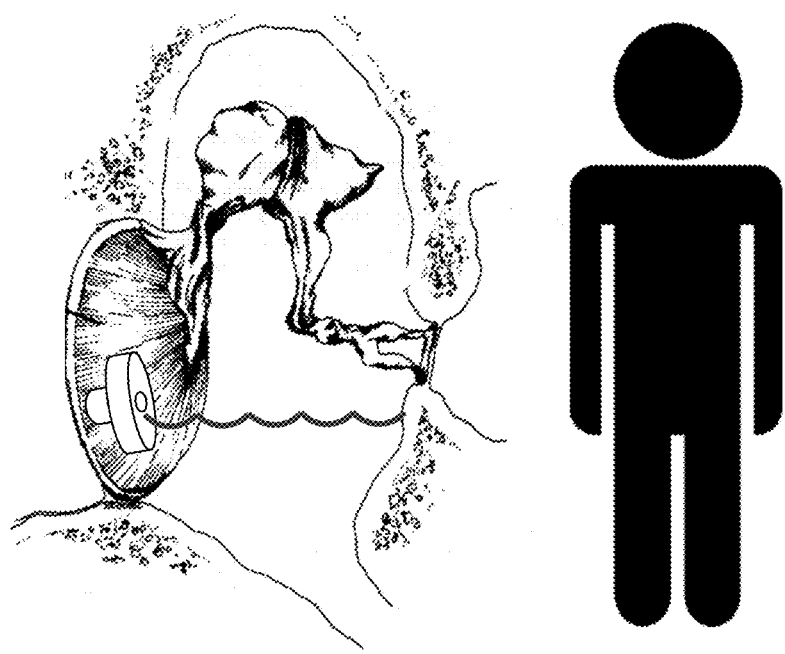
FIG. 11A shows a middle ear of a person in an upright position, with the middle ear cavity partially filled with liquid.

A set of possible anatomical orientations is illustrated in FIGS. 11A, 11B, 11C and 11D. FIG. 11A illustrates a position with the head approximately vertical, as would be the case during typical activities of the patient. With the head in an approximately vertical position, it is possible that liquid may occupy the lower portion of the middle ear cavity, especially if the Eustachian tube is blocked by infection, preventing drainage by that route, as is sometimes the case. It can also be appreciated that the tympanostomy tube provides a limit on the liquid level in the middle ear cavity by providing an exit route for liquid from the middle ear, i.e., liquid can and in the case of otorrhea does drain out through the hole in the tympanostomy tube and drain out through the ear canal of the outer ear. This effectively creates a limit on the level of the liquid in the middle ear, at least in an overall sense. It can be appreciated that the limitation on liquid level is not imposed instantaneously because of factors involving the small size of the hole in the ear tube, viscosity of the exudate liquid, and perhaps surface tension, that may make the drainage of such liquid through the tympanostomy tube less rapid than it otherwise might be. Nevertheless, the presence of the exit path through the tympanostomy tube implies the possibility of a liquid level and an air interface such that the middle ear is partially and only partially filled with liquid. FIG. 11A illustrates such a situation with liquid in the middle ear cavity existing up to approximately the level of the hole in the tympanostomy tube.

Figure 11B:
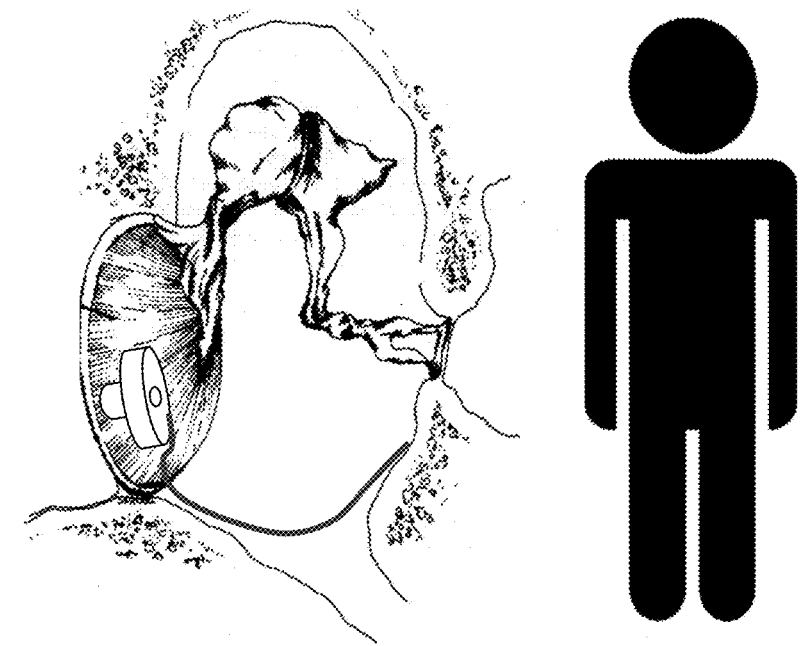
FIG. 11B shows the same situation with only a liquid film present.

FIG. 11B illustrates a similar orientation as FIG. 11A, but with only a liquid film.

FIG. 11C illustrates a situation with the patient lying, with the affected ear facing downward. The tympanostomy tube becomes submerged in the liquid.

FIG. 11D illustrates a similar orientation as FIG. 11C, but with only a liquid film present.

Figure 9:
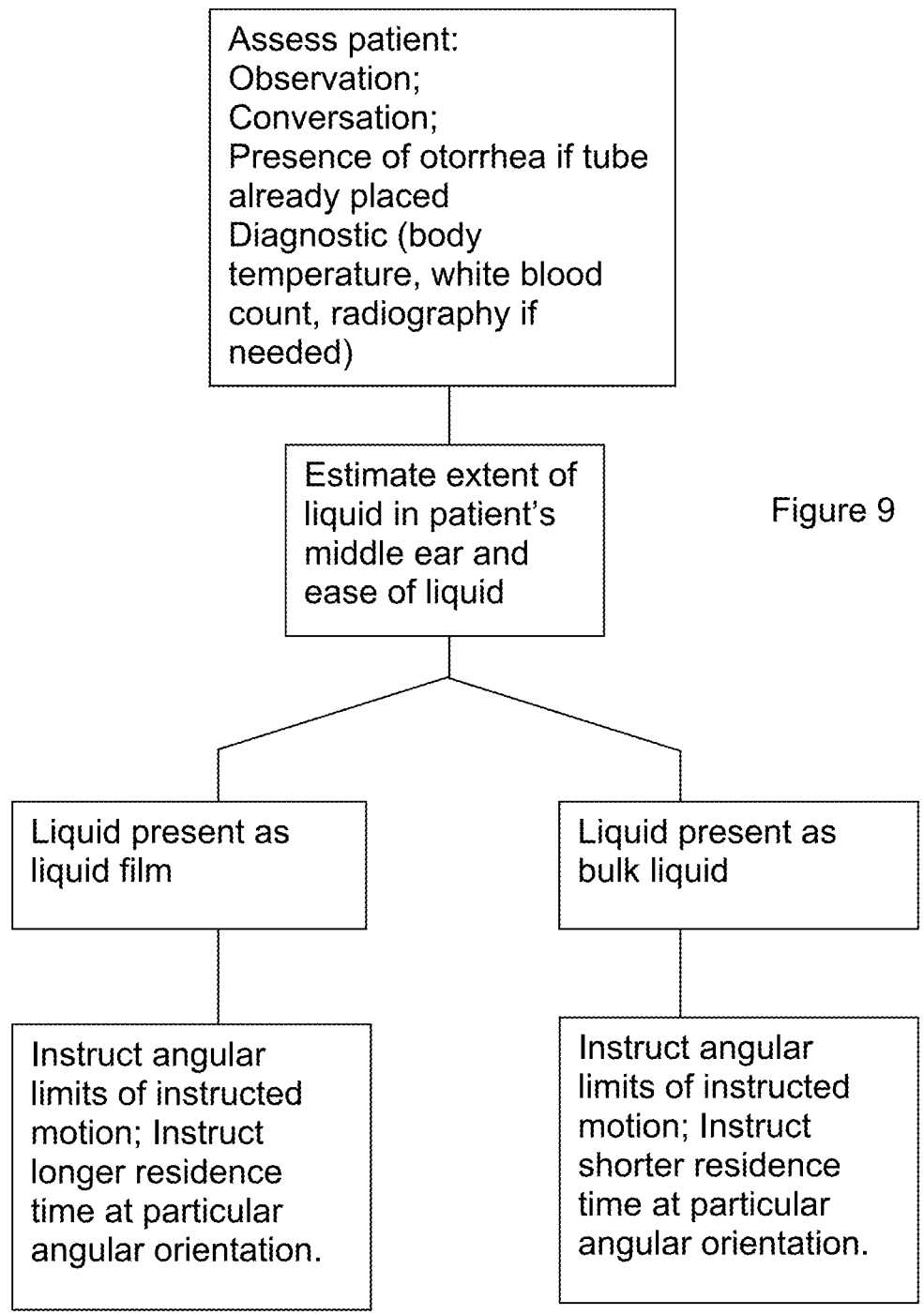
FIG. 9 shows a flowchart or decision tree usable in connection with instructed motion.

Referring now to FIG. 9, deciding on a sequence of reorienting the afflicted part of the patient's body can rest in part on a diagnosis of what is the condition inside the patient's ear, more specifically how much liquid is or is not present in the patient's middle ear. A common way of judging might be ordinary clinical observations such as reports of pain, the patient's behavior, the patient's body temperature, the patient's white blood cell count, and similar indicators. Further, a patient who already has an ear tube implanted might have drainage of fluid out of the ear (otorrhea). Yet another possibility is the use of radiology or ultrasound. However it is obtained, an assessment or estimate of the amount of liquid such as exudate present in the patient's ear can lead to an assessment of what bodily positions and sequence of bodily positions could lead to a desired wetting and de-wetting sequence and associated fluid transport of drug from the ear tube to other surfaces of the middle ear. In particular, it can lead to an assessment of whether there needs to be a hold time for holding the head in certain positions in order to wait for a liquid film that may be somewhat thin and slow-moving to reach a new equilibrium configuration upon assumption of a new bodily position. If the liquid condition is a liquid film, this may require a hold time at individual instructed bodily positions. On the other hand, if the middle ear cavity is partially full of liquid, this may allow a short or almost no hold time for a particular instructed bodily position.

If it is concluded that the amount of liquid in the middle ear cavity is relatively small providing liquid more in the nature of a liquid film rather than bulk liquid, then the instructed motion could include a waiting period at some of the instructed positions, to allow the liquid time to re-orient itself. On the other hand, if it is concluded that there is a moderate amount of liquid in the middle ear cavity providing liquid more in the nature of bulk liquid rather than a liquid film, it might not be so important to include a waiting period at some of the instructed positions.

For example, in the sequence of events involving drug transfer and liquid motion, there can be certain interactions or certain steps that are more limiting in the overall process than are certain other interactions or steps. In such a case, it is useful to know which interaction or step is limiting, in order to design an effective cycle.

It is also possible that diffusion or dissolution where liquid contacts the surface of the implant might be a limiting interaction or step. If that is the case, it is possible that the exposed surface area of the implant that is exposed to the liquid could be increased through texturing or patterning of the surface that the liquid is exposed to. It is still further possible that such texturing or patterning could be designed so as to affect the wetting behavior of the exposed surface when the exposed surface interacts with the liquid, such as by creating a wicking action when liquid contacts the exposed surface.

FIG. 11E illustrates a possible instructed sequence of positions, involving rotating the head back and around the spinal axis while the patient's torso is in an upright position. This could urge fluid, by centrifugal force, radially outward relative to the spinal axis or the center of the head. Such a motion could be performed rapidly enough to generate centrifugal force. Such instructed motion would be applicable for a partially full middle ear cavity rather than a liquid film situation. Rotating the head around the spinal axis is believed to be beneficial in the sense that it could create centrifugal force that urges liquid into contact with the tympanic membrane. If the instructed motion includes rotating the head around the spinal axis, it is possible that this could provide centrifugal force that urges middle ear liquid away from the centerline of the body, toward the eardrum. Such motion would help to wet the flange of the tympanostomy tube, if it has not already been wetted for other reasons. That same liquid could then settle downward when the rotating of the head stops.

FIG. 11F illustrates the head right and left in the form of tilting the head to the right and the left at about 45 degrees or more. This is expected to produce motion or mixing of liquid in the middle ear and thus may be effective in transporting the drug-loaded liquid to remote regions of the cavity. If the middle ear cavity is believed to contain liquid film, a waiting time at the various tilted positions may be appropriate. If the middle ear cavity is believed to contain bulk liquid, waiting times at the positions could be relatively short.

FIG. 11G illustrates a sequence of bodily positions involving the patient lying on the side, lying face up and lying face down. This can also move fluid around the middle ear cavity including in some positions exposing the fluid to the drug available from the tympanostomy tube, while in other positions delivering the drug-laden liquid to other regions of the middle ear cavity. Waiting times can be recommended as already described.

A motion such as nodding, i.e., moving the head forward and backward with the torso in a generally upright position, which is not illustrated, is believed to be less useful than some of the illustrated motions.

Embodiments of the invention are further illustrated, but in no way limited, by the following experimental information.

Experimentally Measured Drug Release

Figure 12:
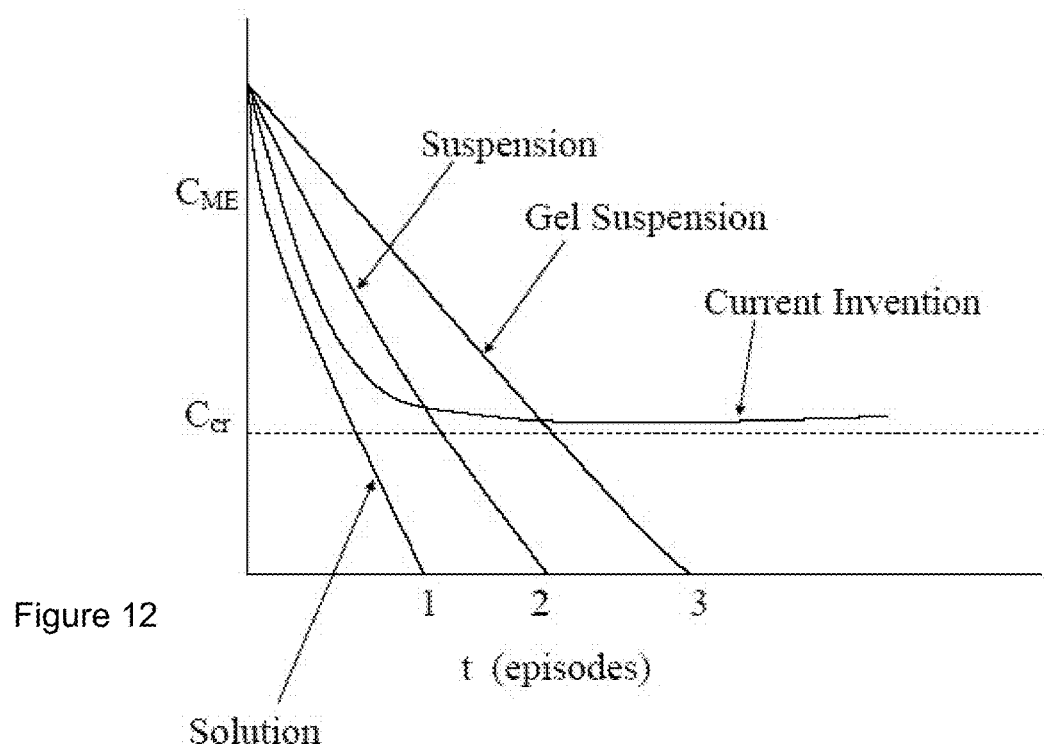
FIG. 12 shows qualitative drug release curves for solution, for suspension, for gel suspension, and for embodiments of the invention.

Referring now to FIG. 12, there is shown schematically a comparison among various drug delivery technologies pertinent to treating otitis media. The vertical axis represents the concentration of drug in the liquid in the middle ear, designated CME. The dotted line represents Ccr, which is a critical concentration of drug in the middle ear fluid that is needed kill bacteria. Represented on the graph are four drug delivery technologies. A technology of delivering liquid containing drug dissolved therein is able to deliver drug, but the drug concentration remains above the critical concentration only for a limited amount of time. In the technology of a suspension, in which particles of undissolved drug are suspended in the liquid, it is possible to maintain the critical concentration for a somewhat longer time because the suspended particles represent a form of reservoir of the drug that can be dissolved if the liquid itself becomes diluted by the generation of new exudate or for any other reason. Yet another form of drug delivery is with a gel suspension. This retains the advantage just described for the suspension form of the drug, and improves on it by virtue of the properties of the gel. The gel helps to maintain the drug in the desired location, because the gel is less easy to dilute and less likely to flow away. Typically a gel suspension is sufficient to treat otitis media for 7 days after myringotomy. However, gel is only deliverable one time, during surgery, because the gel is so viscous that it cannot pass through the central hole in the tympanostomy tube.

Finally, on the same graph is shown the type of result achievable by embodiments of the invention. In embodiments of the invention, the implant may serve as a reservoir of the drug, which emits drug as needed sufficient to maintain at least a desired concentration of drug in the middle ear fluid, and the amount of drug contained in the reservoir is sufficient to maintain that release for a much longer time than is possible with any individual dose or administration of drug in conventional modes such as liquid or gel. It can be noted that in embodiments of the invention, the fraction of the implant that is made of drug can be in the range of 20% by weight, whereas in liquids and suspensions and gels, the concentration of drug in the administered liquid or gel is typically not more than 0.3% by weight. Thus, a larger reservoir of drug is available at the treatment site, and yet the implant performs so that the drug is only released gradually and even that gradual release happens only when needed as indicted by the presence of liquid such as exudate in the middle ear.

Polydispersity index is a description of how wide is the distribution of particle sizes in an aggregate. A monodisperse aggregate (all particles the same size) would have a very small polydispersity index. As the polydispersity index increases, there is a wider spread of particle sizes. In embodiments of the invention, the polydispersity index of the particles of drug may be greater than 0.5, or even greater than 1. It is believed that a larger polydispersity index is preferred. It is believed that having a variety of particle sizes means that as solid particles of drug erode or are leached out, the particles do not all disappear simultaneously (which would give a sharp change of release characteristic if it were to happen). Some solid particles last longer than other solid particles, which is believed to help maintain a sustained release rate for many days.

Figure 13:
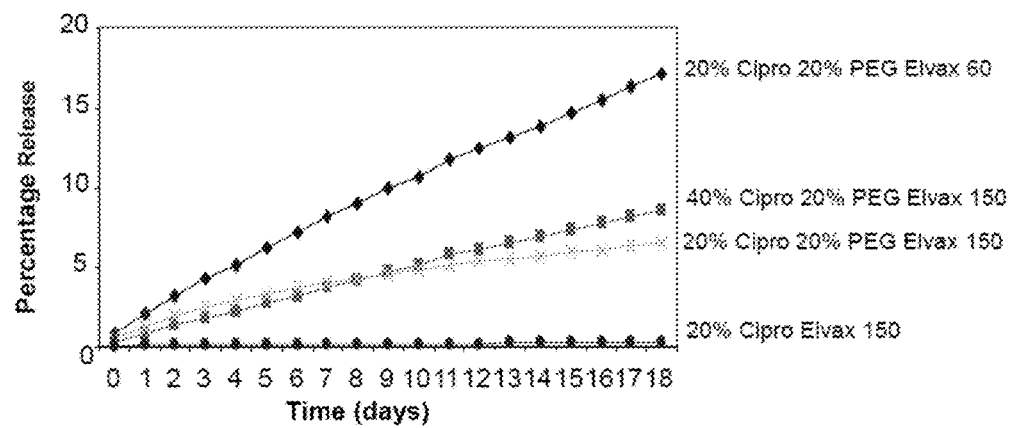
FIG. 13 shows experimental drug release data, obtained in vitro, for various compositions of polymer and drug content.

Referring now to FIG. 13, this in vitro experimental result is obtained by immersing test coupons containing polymeric material and drug in water and measuring the cumulative amount of drug released to the water over an 18-day period. Various different compositions were tested. All of them contained drug, but in some cases different amounts of drug. All of the compositions contained some form of the nonresorbable copolymer elvax (ethylene vinyl acetate). Three of the compositions additionally contained the water-soluble polymer polyethylene glycol, while one of the compositions did not contain polyethylene glycol. It can be seen that the presence of polyethylene glycol significantly improves diffusion and release of the drug, because the sample without any PEG showed extremely slow release. Adding the PEG produced a faster (as desired) drug release. Increasing the drug content produced only a slight additional increase in drug release, and finally adjusting the composition of the ethylene vinyl acetate produced a further increase in drug release.

Figure 14:
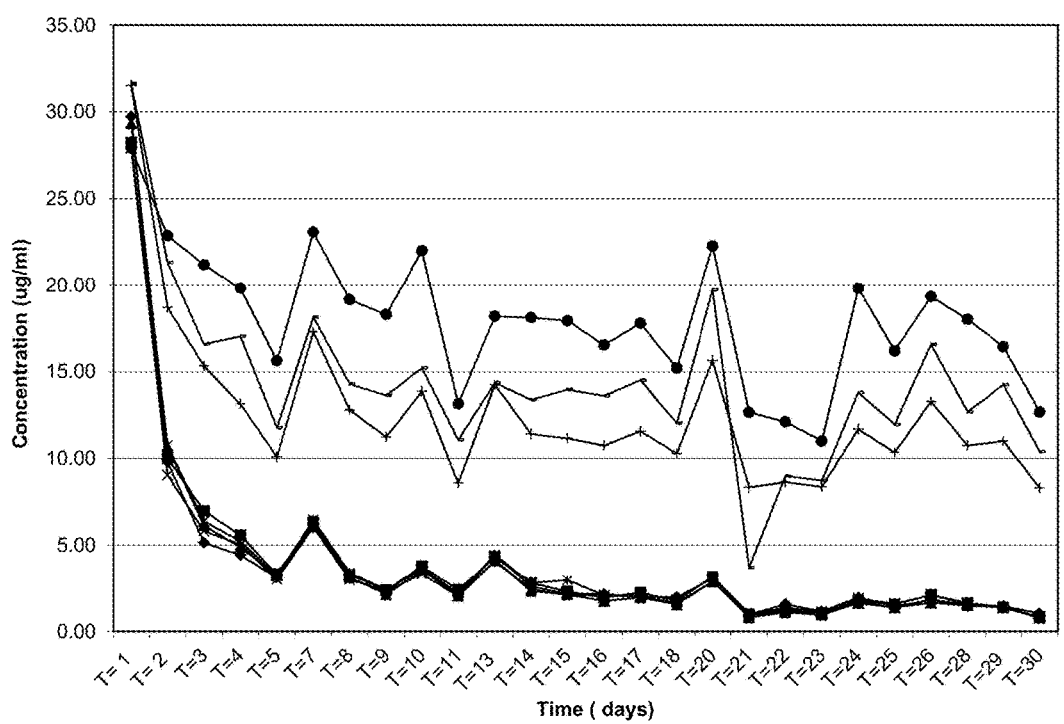
FIG. 14 shows the experimental in vitro results showing the concentration of released drug, with the contacting liquid being changed daily

Referring now to FIG. 14, there are shown experiments for an in vitro situation in which test coupons were exposed to water that was changed every day for 30 consecutive days. This is to simulate 30 episodes of treating otitis media or at least episodes of the beginning stages of otitis media. The lower cluster of nearly-overlapping curves was obtained for tympanostomy tubes that had a total device mass of 4 milligrams and contained 1000 micrograms (1 milligram) of ciprofloxacin. The upper cluster of curves was obtained for tympanostomy tubes that had a total device mass of 10 milligrams and contained 2000 micrograms (2 milligrams of ciprofloxacin. All of the ciprofloxacin was ciprofloxacin betaine. The quantity of water introduced at each water change was 0.5 cubic centimeters, typical of a partially full middle ear cavity.

At the end of the period of testing, even for the smaller size devices, still the concentration of drug attained in the solution after each water change was around 2 micrograms per milliliter, which is more than 10 times the MIC for various microorganisms. This demonstrates the ability of embodiments of the invention to provide sustained ability to deliver enough drug to create a drug concentration well above MIC in water typical of the middle ear cavity, on repeated occasions.

Experiments Using a Chinchilla Model

Figure 15:
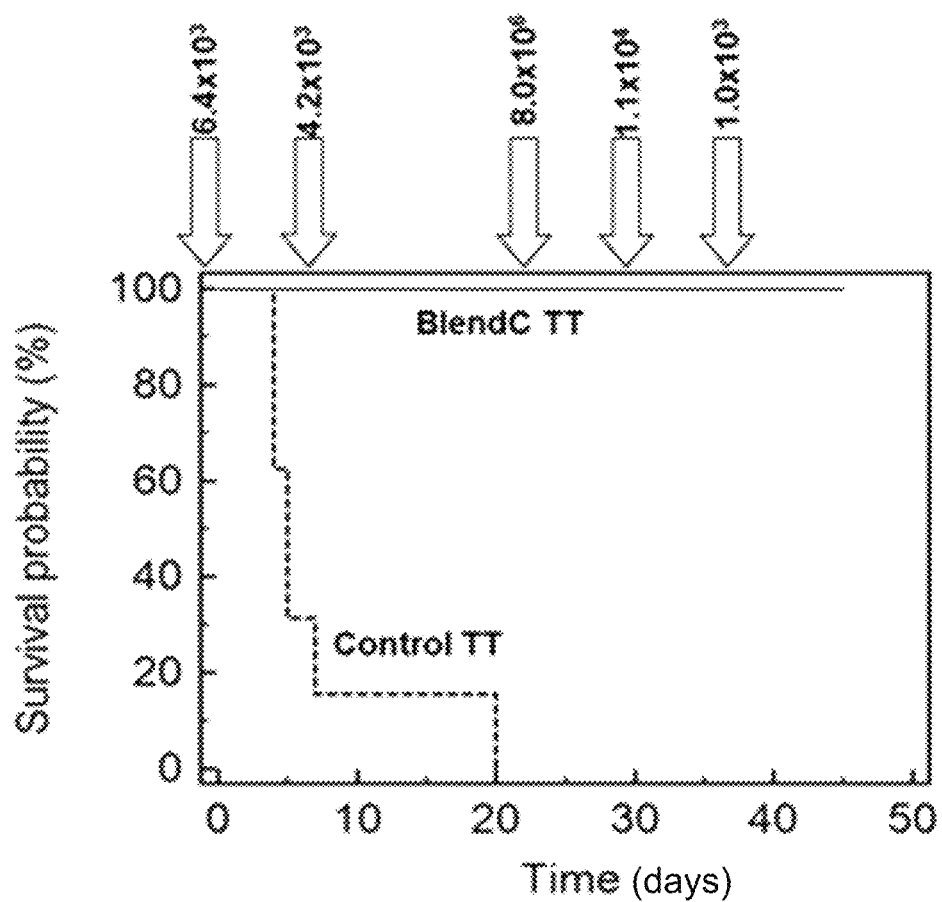
FIG. 15 shows data from an animal model using chinchillas, indicating animal survival for two different groups.

Referring now to FIG. 15, experiments with a chinchilla animal model have provided strong evidence of the bioactivity of the device of embodiments of the invention in an animal model. A chinchilla model of Otitis Media was established. As controls, conventional tympanostomy tubes were implanted into tympanic membranes of chinchillas. As the experiment, tymmpanostomy tubes of an embodiment of the invention were implanted into tympanic membranes of chinchillas. Then, the middle ear of both sets of animals was repeatedly challenged (five times) with inocula of a bioluminescent P. aeruginosa delivered transcanal through the tympanostomy tube. This provided that for the tympanostomy tubes of the embodiment of the invention, the tube would have opportunity to release its constituent antimicrobial agent.

This model actually led to the death of all animals implanted with the control tympanostomy tubes. 80% of these deaths occurred after the first challenge before the second challenge, due to meningitis resulting from the spread of the infected liquid exudate. The rest of the deaths occurred after the second challenge before the third challenge. On the other hand, the tympanostomy tube of embodiments of the invention was able to rescue the experimentally-implanted animals were not injured by this deadly situation, and all of the experimentally-implanted animals survived through all five bacterial challenges to the end of the experiment. This is illustrated in FIG. 15, in the form of a Kaplan-Meier plot.

Figure 16:
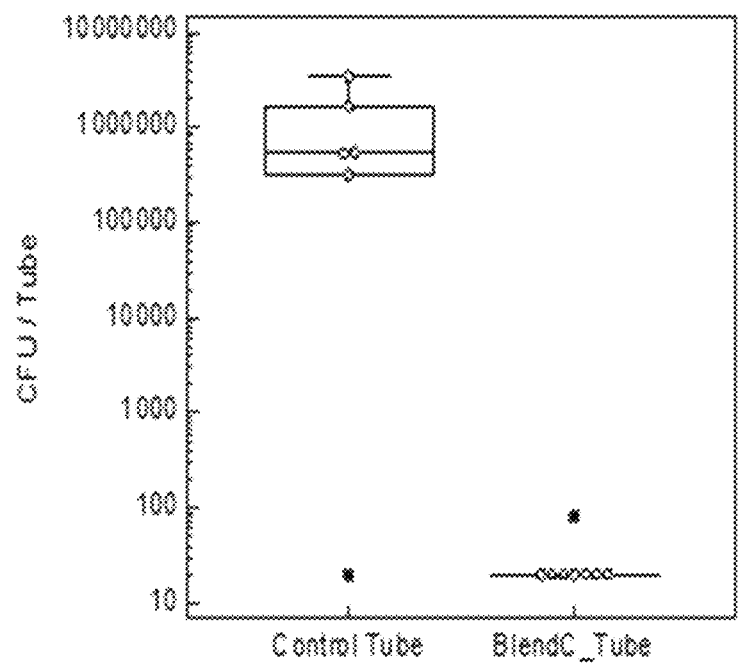
FIG. 16 shows bacterial count on recovered tympanostomy tubes from the control and the experiment.

As another part of the experiment, tympanostomy tubes were recovered from animals in each group and were analyzed for the presence of bacteria. Bacterial counts recovered from the BlendC tubes of embodiments of the invention after 5 challenges over >30 days were some 5 log lower than those recovered from the control tympanostomy tubes collected at the time of animal demise (FIG. 16).

Figure 17:
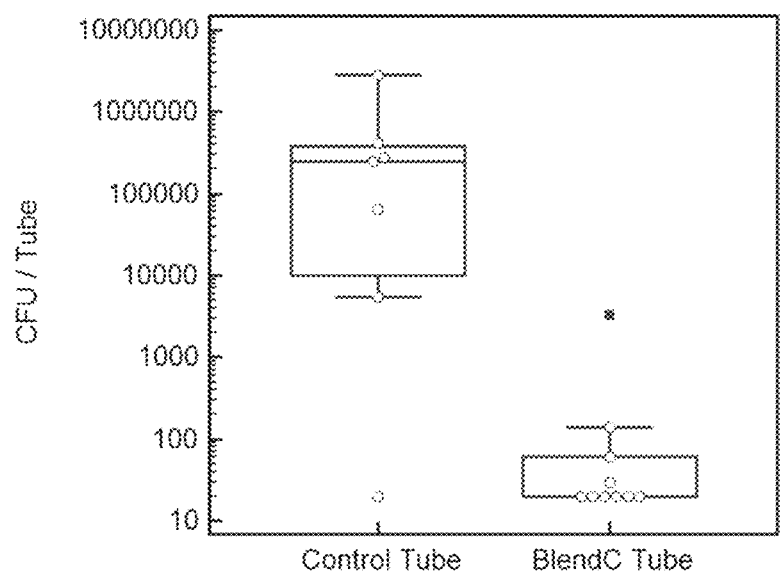
FIG. 17 shows bacterial count on recovered tympanostomy tubes, from a different experiment.

Similar results were seen when chinchillas were subjected to a transbullar (as opposed to transcanal) inoculum with P. aeruginosa, and a comparable reduction in recovered bacteria was seen when a similar protocol was used with a clinical strain of H. influenzae. Although mortality was much reduced in this model with H. influenzae even with control tubes, the BlendC tubes of an embodiment of the invention did reduce it even further (from ~30% to ~15%) (data not shown). FIG. 17 shows that, again, the tubes of embodiments of the invention were effective in eradicating H.flu in animals that were pre-infected before tubes' placement. The bacterial presence on explanted tympanostomy tubes of embodiments of the invention were approximately 3 log lower than those on tympanostomy tubes recovered from the control group.

These results support the conclusion that drug release from the ear tube into the middle ear can prevent several infections and prevent the incidents of Post Tympanostomy Tube Otorrhea. These experimental results and simulations suggest that, using embodiments of the invention, as many as 30 episodes of Otitis Media infections, each having the potential to result in PTTO, may be suppressed according the embodiment of the invention. The tympanostomy tubes of embodiments of the invention do not support growth of bacteria or biofilm on them.

Modeling

As $C_s'(t=0)=C_s$ (Equation 6) and $C_a'(t=0)=C_{as}$ (Equation 7), this allows to obtain useful representation for K $$K = \frac{C_a'(t)}{C_s'(t)} = \frac{C_{a'}(0)}{C_{s'}(0)} = \frac{C_a}{C_{as}} \qquad \text{(Equation 9)}$$

The substitution K according to this equation into Equation (E1.9) transforms the equation for initial fast release in practically more useful form $$M(t) = \frac{D_a C_{as}}{\delta} t \qquad \text{(Equation 10)}$$

It is seen, that the initial rate of release is expressed with Frek, specified for $C_a'(t)=C_{as}$.

As solubility in water $C_{as}$ and $D_a$ are usually known, the equation for fast release contains only shape unknown δ. The equation E1.5 allows to quantify the duration of fast release. The condition (E1.8) determines times, when the release rate is almost invariant. Correspondingly, the condition $$q(2/p)^2 t \sim 1 \qquad \text{(Equation 11)}$$

Determines the time $$t_f = \frac{p^2}{4q} = \left(\frac{\delta^2}{4 D_a^2 D_{as}^2}\right)(DC_s C_o) \qquad \text{(Equation 12)}$$

When decrease in release rate in comparison with

Initial one is not large. The equations (E1.6) are used in derivation. The first product in Equation (12) depends on transport properties of water solution. Second product depends on properties of polymer blend. It is evident, that increase in all three multiplier $C_o$, D, $C_s$ cause increase in duration of fast release. Hence, while maximal value of release rate does not depend on $C_o$, D, $C_s$ and cannot be increased above the value, given by equation (1), the duration of fast release may be essentially increased, if $C_o$, D, $C_s$ are increased simultaneously. This main conclusion agrees with results of our investigation. Initially, the fast release was observed. However, its duration was not sufficient. The systematic work aimed to increase $C_o$, D, $C_s$ resulted in essential prolongation of fast release.

Although regularity revealed in our experiment, agrees with the conclusion of the Higuchi theory regarding fast release and its duration, some results cannot be explained in framework of Higuchi model. One limitation in the Higuchi model is discussed in example 2 because its account explains some of our experimental results and supplements to the prediction of drug release in the Middle Ear.

Limitation of the generalized Higuchi theory regarding modeling initial maximal release mode.

Importance of Drug Particle Dimension and their Size Distribution

Particle size and size distributor are not considered in the Higuchi theory or it is assumed, that they are extremely small. It will be shown: if particle dimension is not very small and if polymer/drug blend is not sufficiently large, then it is possible to have a qualitative discrepancy between experiment and prediction of the Higuchi model for initial release rate. This discrepancy was eliminated in the last stage of our experiment, when the polymer/drug blend was perfected and DCs was increased.

The equation for $C_a'(h)$ may be easily obtained in the framework of the Higuchi model, while $T_r'(h)$ informs how long its deviation from initial $C_a'(h=0)=C_a$ continues. Higuchi postulates quasi-steady evolution even for initial movement, i.e., $h \to 0$. This means a linear distribution for solute concentration within the polymer and within the aqueous solution. This allows a single representation for diffusion flux according to Fick's Law and setting the diffusion fluxes equal to each other at the interface $$\frac{D(C_s - C_s')}{h} = \frac{D_a C_a'}{\delta} \quad (E\ 2.1)$$

Linear profiles of solute concentration are presented on Figure (b), $C_s'$ may be expressed through $C_a'$, taking into account that $$\frac{C_a'}{C_s'} = \frac{C_{as}}{C_s}.$$

This leads to equation for $C_a'$ $$C_a' = \frac{\frac{D}{h} C_s}{\frac{D}{h} \frac{C_s}{C_{as}} + \frac{D_d}{\delta}}$$

Or $$\frac{C_a'}{C_{as}} = \frac{\frac{D}{h} \frac{C_s}{C_{as}}}{\frac{D}{h} \frac{C_s}{C_{as}} + \frac{D_d}{\delta}}$$

The first term in the denominator predominated during initial release, when $h \to 0$, and so the denominator became approximately equal to the numerator. Hence, initially the right hand side of the equation equals 1 and $$C_a' = C_{as} \quad (E2.3)$$

As it follows from the Higuchi model.

With increasing h(t), the first term in denominator plays a smaller role and the second term may dominate. This occurs when $h > h_{cr}$, where $$h_{cr} = \frac{D_s C_s}{D_{as} C_{as}} \delta \quad (E\ 2.4)$$

z.h.s. equals to $0.5\ C_{as}$ $C_a'(h_{cr}) = 0.5\ C_{as}$

Hence, the fast release corresponds to an initial small h in the range $0 < h < h_{cr}$ or to an initial range of time $t < t_f$, where $t_f$ was estimated by equation (12). In agreement with preceding analyses, which lead to Equation (12) Equation (E2.4) shows that increasing in product $D_s C_s$ leads to increase $H_{cr}$, i.e., increase to $t_f$. $N_o$ influence manifests itself at the transition from $h_{cr}$ to $t_f$.

While the Higuchi model leads again to two statements: fast release always exists but its duration may be short, $D_s C_s$ is small account for real dimension of crystals reveals some acceptations.

The uniform crystal distribution means that their mean amount is the same within any plane, parallel interface plane, including the latter It means there are crystals on the interface which dissolve very rapidly due to direct contact with the solution and causes the initial burst. After their dissolution a layer with thickness h=d, where d is the crystal dimension forms The Higuchi model does not account for crystal dimension and may work for $$h > h_{cr2} \sim d \quad (E2.5)$$

When the Higuchi model starts to work $C_a'$ may be determined by substitution $h = h_{cr2} = d$ in equation (E2.2)

$$\frac{C_a'}{C_{as}} = \frac{\frac{D}{h} \frac{C_s}{C_{as}}}{\frac{D}{d} \frac{C_s}{C_{as}} + \frac{D_d}{\delta}} \quad (E\ 2.6)$$

This initial release is twice slower than the maximal release when $$\frac{D}{d} \frac{C_s}{C_{as}} = \frac{D_a}{\delta} \quad (E\ 2.7a)$$

Or $$d \geq \frac{DC_s}{D_a C_{as}} \quad (E\ 2.72)$$

Hence, the initial fast release may be absent with the less-fast release instead of it. If d is sufficiently large, while $DC_s$ is not sufficiently large (polymer/drug is not optimized).

In fact, additional conditions for applicability of the generalized Higuchi theory, including maximal initial release is $$d \leq \frac{DC_s}{D_a C_{as}} \quad (E\ 2.8)$$

This analysis was important because we observed different values for initial release rates. This analysis was important because it shows that we may trust the Higuchi theory and may use it if we account for constraint expressed by equation (E2.8).

It is noteworthy that the Higuchi model may be valid for conditions which are favorable for practical applications, i.e., when the product $DC_s C_o$ is large i.e fast release exists and it is long.

Polydispersity

For example, we may assume that the largest particle dimension is d and it is satisfied to condition (E2.7). Then the initial release is twice weaker than maximal. If there are particles smaller than d, the release will be stronger. While particles with dimension d are connected with water solution and dissolved during burst, that may further decrease the release. This release may be stronger because smaller particles persist and participate in further release.

- large particles dissolved due to contact with water solution. Would be only disfraction of larger particles present the layer with h~d does not contain particles and $C_a' = C_{as}'$, according to equation (E2.6). The presence of smaller particles after burst enhances initial release in case of polydisperse particles.
- Family of kinetic curves (cumulative release) corresponding to polymer drug blend with $(n_0 DC_s)_1 \geq (n_0 DC_s)_2 \geq (n_0 DC_s)_3$ of the same drug according to Higuchi.
- Family of kinetic curves corresponding blend with $(n_0 DC_s)_1 > (n_0 DC_s)_2 > (n_0 DC_s)_3$ according to Higuchi theory supplemented with accent for particle dimension.
- Higuchi model leads invariant initial release rate (universal linear dependence for cumulative release) as on figure A, no matter what is $(D_{cs} n_0)$ value. However the smaller $(D_{cs} n_0)$ value is, the shorter is maximal initial release rate. (Figure A).
- Unfortunately, experiments demonstrate a different initial release rate. This may be explained by influence of the dimension of drug particles as explained in example 2.
- Preparation of Figures A and B based on the microbiologist data is tedious work, which can be postponed. It may transit immediately to Middle Ear filled with exudate using only curve 1, which is the same for A and B.

Main Method

Method to provide drug release into middle ear (ME) due to drug release;

Said method provides drug release above required concentration for over 30 daily challenges Said amount of released drug is provided from implanted device (tab) into ME Transport process inside ME:
- Inflammation develops into liquid (exudates) formation in ME
- Liquid fills entire ME
- Head movements include inertial forces heading to ME:
  - Wall of cavity movement
  - Liquid moves in other direction; opposite of ME wall movement
  - Liquid movement causes effective mixing
  - Liquid moves except near the boundary layer near tube surface Main Release The above process results in a rapid drug release gradient which is proportional to solubility drug diffusivity in water, surface area or tube.

$$\cong \frac{[C_s - C_{bq}]}{\delta} \cdot D_u \cdot S_{tube}$$

The amount of drug released in ME liquid eventually leads to average bulk concentration of drug in ME; this can be estimated by measuring the bulk concentration in ME liquid.

The concentration of drug in ME increases drug release and mixing over a period of time to a saturation level. This saturation level is the solubility limit of drug in water, $C_s$.

However, the concentration of drug in ME or $[C]_{ME}$, is difficult to quantify due to drug losses [adsorption into ME mucosa; metabolism inside ME liquid; drainage through the Eustachian tube If we neglect drug losses to concentration of drug in ME reaches $C_s$, i.e., solubility limit Qualitatively, drug bulk concentration of liquid in ME increases with time. However, drug release will continue to occur because of drug losses. At steady the amount of drug release above $C_s$ is removed due to drug losses At equilibrium, the concentration of drug in ME is determined by rate of drug release from the tube and rate of drug losses from ME. This determines drug concentration in ME at steady state.

Once a concentration gradient is established between drug concentration at tube surface and drug concentration in the bulk of liquid in ME. This gradient $\Delta C$ is proportional to $$\Delta C = [C_{surface} - C_{bulk}] = C_{at\ tube\ surface} \cdot \frac{D_{water}}{\delta} \cdot D_{bulk\ in\ ME}$$

(see exact equation from SSD
A simple equation arises $$C_{in\ ME} \cong C_s \cdot \frac{S_{tube}^{(surface\ area)}}{S_{ME}^{(surface\ area)}}$$

$\left(\text{denominator coefficient is small} \cong \frac{1}{30}\right)$ because $\delta$ cancels out.

The prediction provides concentration in ME≅100 MIC of most organism implanted in causing Otitis Media This is because $C_s$ is about 100 times MIC of main OM organism This is not the case in actual situation due to drug losses; however, accounting for drug losses, $C_{ME}$ will still be 5-30 times MIC in the worst case, when ME is filled with exudates.

In the case of otorrhea, the amount of drug release over 30 or more days (episode) will provide $C_{ME}$ (cipro) that may be sufficient to overcome many episodes of inflammation or infection.

Comparison with Traditional Treatment:

Solution of antibiotic (cipro) will provide concentration up to the solubility limit of the drug in water at the moment when drops are instilled in ME. However, due to drug losses the effective $C_{ME}$ will fall nearly exponentially and will last about one day.

Suspension of antibiotic in water, such as ciprodex will last a little longer, maybe up to 3 days, but will decrease below effective levels due to drug losses. Gel injection will last longer, maybe up to 7 days due to slower dissolution due to gel matrix.

On the other hand, our drug eluding ear tube will last longer, >30-50, or 30-100 episodes of filling and draining of ME.

Additional Comments

It may be appreciated that in conventional treatment, ear tubes are thought of as just a means for ventilation and release of liquid. With embodiments of the invention, the ear tube can be thought of as a drug delivery device that can actively treat Otitis Media. Furthermore, the device will not stop at treating one episode of the disease; rather, after it treats the episode during which it was implanted, the device can serve a prophylactic effect by, without further medical intervention, preventing future early-stage infections from developing into full-blown otitis media, or by, without further medical intervention, treating such a full-blown case of otitis media if the disease reaches such a stage. It is expected that this new therapeutic modality will result in a decrease in the use of oral systemic and topical antibiotics after tympanostomy tube placement.

Notably, the need for topical drops such as Ciprodex® may be eliminated. The implant and method of embodiments of the invention result in a low probability of biofilm growth for the whole time that the tympanostomy tube is in place, and this feature decreases the incidence of post tympanostomy tube otorrhea.

Although embodiments of the invention have been described in relation to the middle ear, it is to be understood that the same principle is applicable to other bodily cavities, and in particular to bodily cavities that are partially filled with liquid or alternately exposed or not exposed to liquid, under at least some circumstances. The following are non-limiting examples of mucosa on which embodiments of the invention can be used: Buccal mucosa; Bronchial mucosa and the lining of vocal folds; Endometrium i.e., the mucosa of the uterus; Esophageal mucosa; Gastric mucosa; Intestinal mucosa; Nasal mucosa; Olfactory mucosa; Oral mucosa; Penile mucosa and Vaginal mucosa.

Polymers that could be used with embodiments of the invention include but are not limited to: Silicone; Polymethylmethacrylate; Hard tissue replacement (HTR) polymer; Polyesters (Dacron, Mersilene); Biodegradable polyesters (polyglycolic acid,poly-l-lactic acid and their copolymers); Polyamides (Supramid, Nylamid); Polyethylene (Medpor); Polypropylene (Prolene, Marlex); Cyanoacrylates; Polytetrafluoroethylene (Teflon, Gore-Tex); Polyurethane; Ethylene vinyl acetate copolymers.

All cited references are incorporated by reference herein in their entirety. Features described herein may be combined in any combination. Steps of a method may be performed in any order that is physically possible. Although embodiments of the invention have been described herein, it is desired that the scope be limited only by the scope of the following claims.

We claim:

1. A device for implantation into a mucosal bodily cavity having a volume of liquid and a volume of air therein, the device comprising:
   a member comprising a polymeric material, a drug, and a surfactant, wherein said polymeric material, said drug, and said surfactant are blended together in a melt and formed into said device, and wherein said polymeric material comprises a substance selected from the group consisting of: polysilicones, silicones, polyurethanes, polyamides, natural rubber, synthetic elastomers, blends thereof, and mixtures thereof;
   wherein said device has a geometry that fits inside but does not completely occupy said mucosal bodily cavity; and
   wherein a surface of said device exhibits a contact angle with pure water that is less than 50 degrees.

2. The device of claim 1, wherein said contact angle is less than 20 degrees.

3. The device of claim 1, wherein said device is a tympanostomy tube having a long direction and having a hole therethrough along said long direction and formed from said member.

4. The device of claim 1, wherein said polymeric material comprises a non-resorbable polymer and a water-soluble polymer.

5. The device of claim 1, wherein said polymeric material or a component of said polymeric material is resorbable.

6. The device of claim 1, wherein said device is porous.

7. The implant of claim 1, wherein said surfactant produces wetting of said device with water or with a secreted liquid, said wetting having a contact angle of from 0 degrees to 10 degrees.

8. The implant of claim 1, wherein said surfactant is selected from the group consisting of: sodium dodecyl sulfate; benzalkonium chloride;
   poloxamer; pluronic; polysorbate; and Tyloxapol.

9. The device of claim 1, wherein said drug comprises a member of the fluoroquinolone family of antibiotics.

10. The device of claim 1, wherein drug comprises ciprofloxacin betaine.

11. The device of claim 10, wherein the drug further comprises ciprofloxacin hydrochloride.

12. The device of claim 1, wherein the member comprises a tubular member formed from said member.

13. The device of claim 1, wherein said surfactant is not ototoxic.

14. The device of claim 1, wherein said surfactant comprises an anionic surfactant, a cationic surfactant, or a nonionic surfactant.

15. The device of claim 1, wherein said surfactant is selected to provide a surface tension on the surface of said device with an exudate of less than 60 dynes/cm.

16. The device of claim 1, wherein said surfactant is selected to provide a surface tension on the surface of said device with an exudate of 60 dynes/cm to 40 dynes/cm.

17. A method of treating a patient, said method comprising:
   (a) implanting a device in a mucosal cavity of the patient, said mucosal cavity having a volume of liquid and a volume of air therein, wherein the device comprises:
   a member comprising a polymeric material, a drug, and a surfactant, wherein said polymeric material, said drug, and said surfactant are blended together in a melt and formed into said device, and wherein said polymeric material comprises a substance selected from the group consisting of: polysilicones, silicones, polyurethanes, polyamides, natural rubber, synthetic elastomers, blends thereof, and mixtures thereof;
   wherein said device has a geometry that fits inside but does not completely occupy said mucosal cavity, and
   wherein a surface of said device exhibits a contact angle with pure water that is less than 50 degrees; and
   (b) causing or instructing said patient to change a bodily orientation of said patient between a first orientation and a second orientation, whereby in one of said orientations at least a portion of said device is exposed to said liquid that is present in said mucosal cavity, and in another of said orientations said device is not exposed to said liquid or is exposed to less of said liquid, whereby said drug is released when said liquid is in contact with said device.

18. The method of claim 17, wherein the member comprises a tubular member formed from said member.

19. The method according to claim 17, wherein said mucosal cavity comprises a middle ear.

20. The method according to claim 17, wherein said mucosal cavity comprises an inner ear.

21. The method according to claim 17, wherein said mucosal cavity comprises a sinus.

22. A device for implantation into a mucosal bodily cavity, said mucosal bodily cavity having a volume of liquid and a volume of air therein, said device comprising:
- a member comprising a polymeric material, a drug, and a surfactant, said polymeric material, said drug, and said surfactant being blended together in a melt;
- wherein said device has a geometry that fits inside but does not completely occupy said mucosal bodily cavity; and
- wherein a surface of said device exhibits a contact angle with pure water that is less than 50 degrees.

23. The device according to claim 22, wherein the member comprises a tubular member.

24. The device of claim 22, wherein said surfactant is not ototoxic.

25. The device of claim 22, wherein said surfactant comprises an anionic surfactant, a cationic surfactant, or a nonionic surfactant.

26. The device of claim 22, wherein said surfactant is selected from the group consisting of: sodium dodecyl sulfate; benzalkonium chloride; poloxamer; pluronic; polysorbate; and Tyloxapol.

27. The device of claim 22, wherein said surfactant is selected to provide a surface tension on the surface of said device with an exudate of less than 60 dynes/cm.

28. The device of claim 22, wherein said surfactant is selected to provide a surface tension on the surface of said device with an exudate of 60 dynes/cm to 40 dynes/cm.

* * * * *